United States Patent [19]

Stevens et al.

[11] Patent Number: 5,955,431
[45] Date of Patent: Sep. 21, 1999

[54] MAST CELL PROTEASE PEPTIDE INHIBITORS

[75] Inventors: Richard L. Stevens, Sudbury; Chifu Huang, Boston, both of Mass.

[73] Assignee: Brigham and Women's Hospital, Inc., Boston, Mass.

[21] Appl. No.: 09/016,366

[22] Filed: Jan. 30, 1998

Related U.S. Application Data

[60] Provisional application No. 60/037,090, Feb. 5, 1997.
[51] Int. Cl.$^6$ .......................... A61K 38/04; A61K 38/05; A61K 38/08
[52] U.S. Cl. .............................. 514/17; 514/18; 530/329; 530/330; 530/331
[58] Field of Search ................................... 530/329–331; 514/17–18

[56] References Cited

U.S. PATENT DOCUMENTS

| | | | |
|---|---|---|---|
| 5,087,564 | 2/1992 | Mai et al. | 435/69.7 |
| 5,187,157 | 2/1993 | Kettner et al. | 514/18 |
| 5,202,239 | 4/1993 | Tarnowski et al. | 435/69.7 |
| 5,239,058 | 8/1993 | Vlasuk et al. | 530/524 |
| 5,372,812 | 12/1994 | Reed et al. | 424/145.1 |
| 5,385,732 | 1/1995 | Anderson et al. | 424/94.64 |
| 5,405,771 | 4/1995 | Anderson et al. | 435/240.2 |
| 5,464,820 | 11/1995 | Burton | 514/16 |
| 5,525,623 | 6/1996 | Spear et al. | 514/423 |
| 5,538,863 | 7/1996 | Price | 435/226 |
| 5,541,087 | 7/1996 | Lo et al. | 435/697 |
| 5,567,602 | 10/1996 | Clark et al. | 435/226 |

FOREIGN PATENT DOCUMENTS

| | | |
|---|---|---|
| PCT/US97/21620 | of 0000 | WIPO . |
| PCT/US98/01865 | of 0000 | WIPO . |
| 9012052 | 10/1990 | WIPO . |
| WO91/02792 | 3/1991 | WIPO . |
| WO94/16083 | 7/1994 | WIPO . |
| WO 94/20527 A1 | 9/1994 | WIPO . |
| WO95/21861 | 8/1995 | WIPO . |
| WO 96/09297 A1 | 3/1996 | WIPO . |
| WO98/24886 | 6/1998 | WIPO . |

OTHER PUBLICATIONS

Ghildval, N., et al., "Fate of Two Mast Cell Tryptases in V3 Mastocytosis and Normal BALB/c Mice Undergoing Passive Systemic Anaphylaxis: Prolonged Retention of Exocytosed mMCP–6 in Connective Tissues, and Rapid Accumulation of Enzymatically Active mMCP–7 in the Blood", *J. Exp. Med.,* (1996), 184:1061–1073.

Matsumoto, R., et al., "Packaging of Proteases and Proteogylcans in the Granules of Mast Cells and Other Hematopoietic Cells",*J Biol. Chem.,* (1995), 270:33:19524–19531.

Braganza, V., et al., "Tryptase from Rat Skin: Pruification and Proerties", *Biochemistry,* (1991), 30:20:4997–5007.

Clark, J., et al., "Tryptase Inhibitors Block Allergen–induced Airway and Inflammatory Responses in Allergic Sheep", *Am J Respir Crit Care Med,* (1995), 152:2076–2083.

Gruber, B., et al., "The Mast Cell as an Effector of Connective Tissue Degradation: A Study of Matrix Susceptibility to Human Mast Cells",*Biochem & Biophys Res Com,* (1990), 171:3:1272–1278.

Cairns, J., et al., "Mast Cell Tryptase Is a Mitogen for Epithelial Cells",*J Immun,* (1996), 156:275–283.

Kielty, C., et al., "Catabolism of Intact Type VI Collagen Microfibrils: Susceptibility To Degradation By Serine Proteinases", *Biochem & Biophys Res Com,* (1993), 191:3:1230–1236.

Kovanen, P., et al., "Infiltrates of Activated Mast Cells at the Site of Coronary Atheromatous Erosion or Rupture in Myocardial Infarction", *Circulation,* (1995), 92:5:1084–1088.

Saarinen, J., et al., "Activation of Human Interstitial Procollagenase through Direct Cleavage of the Leu$^{83}$–Thr$^{84}$ Bond by Mast Cell Chymase",*J Bio Chem,* (1994), 269:27:18134–18140.

DuBuske, L., et al., "Granule–Associated Serine Neutral Proteases of the Mouse Bone Marrow–Derived Mast Cell That Degrade Fibronectin: Their Increases After Sodium Butyrate Treatment of the Cells", *J Immun,,* (1984), 133:3:1535–1541.

Constantinides, P., et al., "Infiltrates of Activated Mast Cells at the Site of Coronary Atheromatous Erosion or Rupture in Myocardial Infaction", *Circulation,*(1995), 92:1083.

Leighton et al. FEBS Lett. 375(3), 289–93, Mar. 1995.

Zhi–mei Wang, et al., "Production of Active Recombinant Human Chymase from a Construct Containing the Enterokinase Cleavage Site of Trypsinogen in Place of the Native Propeptide Sequence," Biol. Chem. Hoppe–Seyler, (1995), vol. 376, pp. 681–684.

Bajusz, S., Peptide Inhibitors of Trypsin–Like Enzymes, Symposia Biologica Hungarica 25; pp. 279–298, (1984).

Jouko Lohi et al., Pericellular Substrates of Human Mast Cell Tryptase: 72,000 Dalton Gelatinase and Fibronectin, Journal of Cellular Biochem., 50:337–349 (1992).

Beat Steiner et al., Peptides Derived from a Sequence within $\beta_2$ Integrin Bind to Platelet $\alpha_{IIb}\beta\_$(GPIIIb–IIIa) and Inhibit Ligand Binding, J. of Biological Chem. 268, No. 10, Apr. 5, 1993, pp. 6870–6873.

Rami Herskoviz et al., Nonpeptidic Analogues of the Arg–Gly–Asp (RGD) Sequence Specifically Inhibit the Adhesion of Human Tenon's Capsule Fibroblasts to Fibronectin, Investigative Opthalmology & Visual Science, vol. 35, No. 5, Apr. 1994, pp. 2585–2591.

(List continued on next page.)

*Primary Examiner*—Cecilia J. Tsang
*Assistant Examiner*—Michael Borin
*Attorney, Agent, or Firm*—Wolf, Greenfield & Sacks P.C.

[57] ABSTRACT

Compositions and methods for inhibiting a complex containing a mast cell protease are provided. The compositions are useful for treating inflammatory disorders, such as asthma, that are mediated by release of a tryptase-6 protein. Methods for identifying additional specific inhibitors of a complex containing tryptase-6 protein and a serglycin glycosaminoglycan also are provided.

21 Claims, No Drawings

OTHER PUBLICATIONS

McNeil, H.P., et al., Isolation, characterizatin, and transcription of the gene encoding mouse mast cell protease 7, Dec. 1992, vol. 89, pp. 11174–11178.

Schwartz, L., et al., "Effect of Tryptase . . . ", *J Allergy Clin Immunol*, (1985), 75 (1 Part 2) Abstract.

Ryan, T., et al., "Urticaria and fibrinolysis", *Clin Exp Dermatol*, (1977), 2:2:177–182 Abstract.

Forsberg, G., et al., "An evaluation of . . . ", *J Protein Chem*, (1992), 11:2:201–211 Abstract.

Light, A., et al., "The amino–terminal . . . ", *J. Protien Chem*, (1991), 10:5:475–480 Abstract.

Martinez, A., et al., "Expression of recombinant . . . ", *Biochem J.*, (1995), 306(Pt 2): 589–597 Abstract.

Su, X., et al., "Production of recombinant . . . ", *Biotechniques*, (1992), 12:5:756–762 Abstract.

Kuhn, S., et al., "The baculovirus expression . . . ", *Gene*, (1995), 162:2:225–229 Abstract.

Kroll, D., et al., "A multifunctional prokaryotic . . . ", *DNA Cell Biol*, 12:5:441–453 Abstract.

Dobrynin, V., et al., "Chemical–enzymatic . . . ", *Bioorg Khim*, (1989), 15:9:1232–1238 Abstract.

Scheele, G., et al., "Proteolytic processing . . . ", *J Biol Chem*, (1983), 258:3:2005–2009 Abstract.

SEQUENCE LISTING (1) GENERAL INFORMATION:

(iii) NUMBER OF SEQUENCES: 65

(2) INFORMATION FOR SEQ ID NO:1:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Arg Asn Arg Gln Lys Thr
1               5

(2) INFORMATION FOR SEQ ID NO:2:

(i) SEQUENCE CHARACTERISTICS:
        (A) LENGTH: 3 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Arg Asn Arg
1

(2) INFORMATION FOR SEQ ID NO:3:

```
        (i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Arg Asn Arg Gln
1

(2) INFORMATION FOR SEQ ID NO:4:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Arg Asn Arg Gln Lys
1               5

(2) INFORMATION FOR SEQ ID NO:5:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Asn Arg Gln Lys Thr
1               5

(2) INFORMATION FOR SEQ ID NO:6:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Arg Gln Lys Thr
1

(2) INFORMATION FOR SEQ ID NO:7:

(i) SEQUENCE CHARACTERISTICS:
            (A) LENGTH: 3 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Gln Lys Thr
1

(2) INFORMATION FOR SEQ ID NO:8:
```

(i) SEQUENCE CHARACTERISTICS:
            (A) LENGTH: 3 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Arg Gln Lys
1

(2) INFORMATION FOR SEQ ID NO:9:

(i) SEQUENCE CHARACTERISTICS:
            (A) LENGTH: 3 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

Asn Arg Gln
1

(2) INFORMATION FOR SEQ ID NO:10:

(i) SEQUENCE CHARACTERISTICS:
            (A) LENGTH: 3 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:10:

Arg Gln Lys
1

(2) INFORMATION FOR SEQ ID NO:11:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Arg Gln Arg Gln Lys Thr
1               5

(2) INFORMATION FOR SEQ ID NO:12:

(i) SEQUENCE CHARACTERISTICS:
            (A) LENGTH: 2386 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:12:

Met Leu Arg Gly Pro Gly Pro Gly Leu Leu Leu Leu Ala Val Leu Cys
1               5                   10                  15

Leu Gly Thr Ala Val Pro Ser Thr Gly Ala Ser Lys Ser Lys Arg Gln
            20                  25                  30

-continued

```
Ala Gln Gln Met Val Gln Pro Gln Ser Pro Val Ala Val Ser Gln Ser
         35                  40                  45

Lys Pro Gly Cys Tyr Asp Asn Gly Lys His Tyr Gln Ile Asn Gln Gln
 50                  55                  60

Trp Glu Arg Thr Tyr Leu Gly Asn Val Leu Val Cys Thr Cys Tyr Gly
 65                  70                  75                  80

Gly Ser Arg Gly Phe Asn Cys Glu Ser Lys Pro Glu Ala Glu Glu Thr
                 85                  90                  95

Cys Phe Asp Lys Tyr Thr Gly Asn Thr Tyr Arg Val Gly Asp Thr Tyr
             100                 105                 110

Glu Arg Pro Lys Asp Ser Met Ile Trp Asp Cys Thr Cys Ile Gly Ala
         115                 120                 125

Gly Arg Gly Arg Ile Ser Cys Thr Ile Ala Asn Arg Cys His Glu Gly
 130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                 165                 170                 175

Trp Thr Cys Lys Pro Ile Ala Glu Lys Cys Phe Asp His Ala Ala Gly
             180                 185                 190

Thr Ser Tyr Val Val Gly Glu Thr Trp Glu Lys Pro Tyr Gln Gly Trp
         195                 200                 205

Met Met Val Asp Cys Thr Cys Leu Gly Glu Gly Ser Gly Arg Ile Thr
 210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                 245                 250                 255

Gln Cys Ile Cys Thr Gly Asn Gly Arg Gly Glu Trp Lys Cys Glu Arg
             260                 265                 270

His Thr Ser Val Gln Thr Thr Ser Ser Gly Ser Gly Pro Phe Thr Asp
         275                 280                 285

Val Arg Ala Ala Val Tyr Gln Pro Gln Pro His Pro Gln Pro Pro Pro
 290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                 325                 330                 335

Gly Asn Gly Val Ser Cys Gln Glu Thr Ala Val Thr Gln Thr Tyr Gly
             340                 345                 350

Gly Asn Ser Asn Gly Glu Pro Cys Val Leu Pro Phe Thr Tyr Asn Gly
         355                 360                 365

Arg Thr Phe Tyr Ser Cys Thr Thr Glu Gly Arg Gln Asp Gly His Leu
 370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Gln Gly Gly Asn Ser Asn
                 405                 410                 415

Gly Ala Leu Cys His Phe Pro Phe Leu Tyr Asn Asn His Asn Tyr Thr
             420                 425                 430

Asp Cys Thr Ser Glu Gly Arg Arg Asp Asn Met Lys Trp Cys Gly Thr
         435                 440                 445
```

```
Thr Gln Asn Tyr Asp Ala Asp Gln Lys Phe Gly Phe Cys Pro Met Ala
        450                 455                 460
Ala His Glu Glu Ile Cys Thr Thr Asn Glu Gly Val Met Tyr Arg Ile
465                 470                 475                 480
Gly Asp Gln Trp Asp Lys Gln His Asp Met Gly His Met Met Arg Cys
                    485                 490                 495
Thr Cys Val Gly Asn Gly Arg Gly Glu Trp Thr Cys Tyr Ala Tyr Ser
            500                 505                 510
Gln Leu Arg Asp Gln Cys Ile Val Asp Ile Thr Tyr Asn Val Asn
        515                 520                 525
Asp Thr Phe His Lys Arg His Glu Glu Gly His Met Leu Asn Cys Thr
        530                 535                 540
Cys Phe Gly Gln Gly Arg Gly Arg Trp Lys Cys Asp Pro Val Asp Gln
545                 550                 555                 560
Cys Gln Asp Ser Glu Thr Gly Thr Phe Tyr Gln Ile Gly Asp Ser Trp
                565                 570                 575
Glu Lys Tyr Val His Gly Val Arg Tyr Gln Cys Tyr Cys Tyr Gly Arg
            580                 585                 590
Gly Ile Gly Glu Trp His Cys Gln Pro Leu Gln Thr Tyr Pro Ser Ser
        595                 600                 605
Ser Gly Pro Val Glu Val Phe Ile Thr Glu Thr Pro Ser Gln Pro Asn
610                 615                 620
Ser His Pro Ile Gln Trp Asn Ala Pro Gln Pro Ser His Ile Ser Lys
625                 630                 635                 640
Tyr Ile Leu Arg Trp Arg Pro Lys Asn Ser Val Gly Arg Trp Lys Glu
                645                 650                 655
Ala Thr Ile Pro Gly His Leu Asn Ser Tyr Thr Ile Lys Gly Leu Lys
            660                 665                 670
Pro Gly Val Val Tyr Glu Gly Gln Leu Ile Ser Ile Gln Gln Tyr Gly
        675                 680                 685
His Gln Glu Val Thr Arg Phe Asp Phe Thr Thr Thr Ser Thr Ser Thr
        690                 695                 700
Pro Val Thr Ser Asn Thr Val Thr Gly Glu Thr Thr Pro Phe Ser Pro
705                 710                 715                 720
Leu Val Ala Thr Ser Glu Ser Val Thr Glu Ile Thr Ala Ser Ser Phe
                725                 730                 735
Val Val Ser Trp Val Ser Ala Ser Asp Thr Val Ser Gly Phe Arg Val
            740                 745                 750
Glu Tyr Glu Leu Ser Glu Glu Gly Asp Glu Pro Gln Tyr Leu Asp Leu
        755                 760                 765
Pro Ser Thr Ala Thr Ser Val Asn Ile Pro Asp Leu Leu Pro Gly Arg
770                 775                 780
Lys Tyr Ile Val Asn Val Tyr Gln Ile Ser Glu Asp Gly Glu Gln Ser
785                 790                 795                 800
Leu Ile Leu Ser Thr Ser Gln Thr Thr Ala Pro Asp Ala Pro Pro Asp
                805                 810                 815
Pro Thr Val Asp Gln Val Asp Asp Thr Ser Ile Val Val Arg Trp Ser
            820                 825                 830
Arg Pro Gln Ala Pro Ile Thr Gly Tyr Arg Ile Val Tyr Ser Pro Ser
        835                 840                 845
Val Glu Gly Ser Ser Thr Glu Leu Asn Leu Pro Glu Thr Ala Asn Ser
        850                 855                 860
Val Thr Leu Ser Asp Leu Gln Pro Gly Val Gln Tyr Asn Ile Thr Ile
865                 870                 875                 880
```

-continued

Tyr Ala Val Glu Glu Asn Gln Glu Ser Thr Pro Val Val Ile Gln Gln
              885                 890                 895

Glu Thr Thr Gly Thr Pro Arg Ser Asp Thr Val Pro Ser Pro Arg Asp
          900                 905                 910

Leu Gln Phe Val Glu Val Thr Asp Val Lys Val Thr Ile Met Trp Thr
          915                 920                 925

Pro Pro Glu Ser Ala Val Thr Gly Tyr Arg Val Asp Val Ile Pro Val
          930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
              965                 970                 975

Val Phe Ala Val Ser His Gly Arg Glu Ser Lys Pro Leu Thr Ala Gln
              980                 985                 990

Gln Thr Thr Lys Leu Asp Ala Pro Thr Asn Leu Gln Phe Val Asn Glu
              995                 1000                1005

Thr Asp Ser Thr Val Leu Val Arg Trp Thr Pro Pro Arg Ala Gln Ile
          1010                1015                1020

Thr Gly Tyr Arg Leu Thr Val Gly Leu Thr Arg Arg Gly Gln Pro Arg
025                 1030                1035                1040

Gln Tyr Asn Val Gly Pro Ser Val Ser Lys Tyr Pro Leu Arg Asn Leu
              1045                1050                1055

Gln Pro Ala Ser Glu Tyr Thr Val Ser Leu Val Ala Ile Lys Gly Asn
              1060                1065                1070

Gln Glu Ser Pro Lys Ala Thr Gly Val Phe Thr Thr Leu Gln Pro Gly
              1075                1080                1085

Ser Ser Ile Pro Pro Tyr Asn Thr Glu Val Thr Glu Thr Thr Ile Val
              1090                1095                1100

Ile Thr Trp Thr Pro Ala Pro Arg Ile Gly Phe Lys Leu Gly Val Arg
105                 1110                1115                1120

Pro Ser Gln Gly Gly Glu Ala Pro Arg Glu Val Thr Ser Asp Ser Gly
              1125                1130                1135

Ser Ile Val Val Ser Gly Leu Thr Pro Gly Val Glu Tyr Val Tyr Thr
              1140                1145                1150

Ile Gln Val Leu Arg Asp Gly Gln Glu Arg Asp Ala Pro Ile Val Asn
              1155                1160                1165

Lys Val Val Thr Pro Leu Ser Pro Pro Thr Asn Leu His Leu Glu Ala
              1170                1175                1180

Asn Pro Asp Thr Gly Val Leu Thr Val Ser Trp Glu Arg Ser Thr Thr
185                 1190                1195                1200

Pro Asp Ile Thr Gly Tyr Arg Ile Thr Thr Thr Pro Thr Asn Gly Gln
              1205                1210                1215

Gln Gly Asn Ser Leu Glu Glu Val Val His Ala Asp Gln Ser Ser Cys
              1220                1225                1230

Thr Phe Asp Asn Leu Ser Pro Gly Leu Glu Tyr Asn Val Ser Val Tyr
              1235                1240                1245

Thr Val Lys Asp Asp Lys Glu Ser Val Pro Ile Ser Asp Thr Ile Ile
              1250                1255                1260

Pro Ala Val Pro Pro Pro Thr Asp Leu Arg Phe Thr Asn Ile Gly Pro
265                 1270                1275                1280

Asp Thr Met Arg Val Thr Trp Ala Pro Pro Pro Ser Ile Asp Leu Thr
              1285                1290                1295

-continued

```
Asn Phe Leu Val Arg Tyr Ser Pro Val Lys Asn Glu Glu Asp Val Ala
            1300                1305                1310

Glu Leu Ser Ile Ser Pro Ser Asp Asn Ala Val Val Leu Thr Asn Leu
            1315                1320                1325

Leu Pro Gly Thr Glu Tyr Val Val Ser Val Ser Val Tyr Glu Gln
            1330                1335                1340

His Glu Ser Thr Pro Leu Arg Gly Arg Gln Lys Thr Gly Leu Asp Ser
345                 1350                1355                1360

Pro Thr Gly Ile Asp Phe Ser Asp Ile Thr Ala Asn Ser Phe Thr Val
            1365                1370                1375

His Trp Ile Ala Pro Arg Ala Thr Ile Thr Gly Tyr Arg Ile Arg His
            1380                1385                1390

His Pro Glu His Phe Ser Gly Arg Pro Arg Glu Asp Arg Val Pro His
            1395                1400                1405

Ser Arg Asn Ser Ile Thr Leu Thr Asn Leu Thr Pro Gly Thr Glu Tyr
            1410                1415                1420

Val Val Ser Ile Val Ala Leu Asn Gly Arg Glu Glu Ser Pro Leu Leu
425                 1430                1435                1440

Ile Gly Gln Gln Ser Thr Val Ser Asp Val Pro Arg Asp Leu Glu Val
            1445                1450                1455

Val Ala Ala Thr Pro Thr Ser Leu Leu Ile Ser Trp Asp Ala Pro Ala
            1460                1465                1470

Val Thr Val Arg Tyr Tyr Arg Ile Thr Tyr Gly Glu Thr Gly Gly Asn
            1475                1480                1485

Ser Pro Val Gln Glu Phe Thr Val Pro Gly Ser Lys Ser Thr Ala Thr
            1490                1495                1500

Ile Ser Gly Leu Lys Pro Gly Val Asp Tyr Thr Ile Thr Val Tyr Ala
505                 1510                1515                1520

Val Thr Gly Arg Gly Asp Ser Pro Ala Ser Ser Lys Pro Ile Ser Ile
            1525                1530                1535

Asn Tyr Arg Thr Glu Ile Asp Lys Pro Ser Gln Met Gln Val Thr Asp
            1540                1545                1550

Val Gln Asp Asn Ser Ile Ser Val Lys Trp Leu Pro Ser Ser Ser Pro
            1555                1560                1565

Val Thr Gly Tyr Arg Val Thr Thr Thr Pro Lys Asn Gly Pro Gly Pro
            1570                1575                1580

Thr Lys Thr Lys Thr Ala Gly Pro Asp Gln Thr Glu Met Thr Ile Glu
585                 1590                1595                1600

Gly Leu Gln Pro Thr Val Glu Tyr Val Val Ser Val Tyr Ala Gln Asn
            1605                1610                1615

Pro Ser Gly Glu Ser Gln Pro Leu Val Gln Thr Ala Val Thr Asn Ile
            1620                1625                1630

Asp Arg Pro Lys Gly Leu Ala Phe Thr Asp Val Asp Val Asp Ser Ile
            1635                1640                1645

Lys Ile Ala Trp Glu Ser Pro Gln Gly Gln Val Ser Arg Tyr Arg Val
            1650                1655                1660

Thr Tyr Ser Ser Pro Glu Asp Gly Ile His Glu Leu Phe Pro Ala Pro
665                 1670                1675                1680

Asp Gly Glu Glu Asp Thr Ala Glu Leu Gln Gly Leu Arg Pro Gly Ser
            1685                1690                1695

Glu Tyr Thr Val Ser Val Val Ala Leu His Asp Asp Met Glu Ser Gln
            1700                1705                1710

Pro Leu Ile Gly Thr Gln Ser Thr Ala Ile Pro Ala Pro Thr Asp Leu
            1715                1720                1725
```

```
Lys Phe Thr Gln Val Thr Pro Thr Ser Leu Ser Ala Gln Trp Thr Pro
    1730                1735                1740

Pro Asn Val Gln Leu Thr Gly Tyr Arg Val Arg Val Thr Pro Lys Glu
745                 1750                1755                1760

Lys Thr Gly Pro Met Lys Glu Ile Asn Leu Ala Pro Asp Ser Ser Ser
                1765                1770                1775

Val Val Val Ser Gly Leu Met Val Ala Thr Lys Tyr Glu Val Ser Val
            1780                1785                1790

Tyr Ala Leu Lys Asp Thr Leu Thr Ser Arg Pro Ala Gln Gly Val Val
    1795                1800                1805

Thr Thr Leu Glu Asn Val Ser Pro Pro Arg Arg Ala Arg Val Thr Asp
    1810                1815                1820

Ala Thr Glu Thr Thr Ile Thr Ile Ser Trp Arg Thr Lys Thr Glu Thr
825                 1830                1835                1840

Ile Thr Gly Phe Gln Val Asp Ala Val Pro Ala Asn Gly Gln Thr Pro
                1845                1850                1855

Ile Gln Arg Thr Ile Lys Pro Asp Val Arg Ser Tyr Thr Ile Thr Gly
                1860                1865                1870

Leu Gln Pro Gly Thr Asp Tyr Lys Ile Tyr Leu Tyr Thr Leu Asn Asp
    1875                1880                1885

Asn Ala Arg Ser Ser Pro Val Val Ile Asp Ala Ser Thr Ala Ile Asp
    1890                1895                1900

Ala Pro Ser Asn Leu Arg Phe Leu Ala Thr Thr Pro Asn Ser Leu Leu
905                 1910                1915                1920

Val Ser Trp Gln Pro Pro Arg Ala Arg Ile Thr Gly Tyr Ile Ile Lys
                1925                1930                1935

Tyr Glu Lys Pro Gly Ser Pro Pro Arg Glu Val Val Pro Arg Pro Arg
                1940                1945                1950

Pro Gly Val Thr Glu Ala Thr Ile Thr Gly Leu Glu Pro Gly Thr Glu
                1955                1960                1965

Tyr Thr Ile Tyr Val Ile Ala Leu Lys Asn Asn Gln Lys Ser Glu Pro
    1970                1975                1980

Leu Ile Gly Arg Lys Lys Thr Asp Glu Leu Pro Gln Leu Val Thr Leu
985                 1990                1995                2000

Pro His Pro Asn Leu His Gly Pro Glu Ile Leu Asp Val Pro Ser Thr
                2005                2010                2015

Val Gln Lys Thr Pro Phe Val Thr His Pro Gly Tyr Asp Thr Gly Asn
                2020                2025                2030

Gly Ile Gln Leu Pro Gly Thr Ser Gly Gln Gln Pro Ser Val Gly Gln
                2035                2040                2045

Gln Met Ile Phe Glu Glu His Gly Phe Arg Arg Thr Thr Pro Pro Thr
    2050                2055                2060

Thr Ala Thr Pro Ile Arg His Arg Pro Arg Pro Tyr Pro Pro Asn Val
065                 2070                2075                2080

Gly Glu Glu Ile Gln Ile Gly His Ile Pro Arg Glu Asp Val Asp Tyr
                2085                2090                2095

His Leu Tyr Pro His Gly Pro Gly Leu Asn Pro Asn Ala Ser Thr Gly
    2100                2105                2110

Gln Glu Ala Leu Ser Gln Thr Thr Ile Ser Trp Ala Pro Phe Gln Asp
    2115                2120                2125

Thr Ser Glu Tyr Ile Ile Ser Cys His Pro Val Gly Thr Asp Glu Glu
    2130                2135                2140
```

```
Pro Leu Gln Phe Arg Val Pro Gly Thr Ser Thr Ser Ala Thr Leu Thr
145                 2150                2155                2160

Gly Leu Thr Arg Gly Ala Thr Tyr Asn Ile Ile Val Glu Ala Leu Lys
            2165                2170                2175

Asp Gln Gln Arg His Lys Val Arg Glu Glu Val Val Thr Val Gly Asn
        2180                2185                2190

Ser Val Asn Glu Gly Leu Asn Gln Pro Thr Asp Asp Ser Cys Phe Asp
    2195                2200                2205

Pro Tyr Thr Val Ser His Tyr Ala Val Gly Asp Glu Trp Glu Arg Met
2210                2215                2220

Ser Glu Ser Gly Phe Lys Leu Leu Cys Gln Cys Leu Gly Phe Gly Ser
225                 2230                2235                2240

Gly His Phe Arg Cys Asp Ser Ser Arg Trp Cys His Asp Asn Gly Val
            2245                2250                2255

Asn Tyr Lys Ile Gly Glu Lys Trp Asp Arg Gln Gly Glu Asn Gly Gln
        2260                2265                2270

Met Met Ser Cys Thr Cys Leu Gly Asn Gly Lys Gly Glu Phe Lys Cys
    2275                2280                2285

Asp Pro His Glu Ala Thr Cys Tyr Asp Asp Gly Lys Thr Tyr His Val
2290                2295                2300

Gly Glu Gln Trp Gln Lys Glu Tyr Leu Gly Ala Ile Cys Ser Cys Thr
305                 2310                2315                2320

Cys Phe Gly Gly Gln Arg Gly Trp Arg Cys Asp Asn Cys Arg Arg Pro
            2325                2330                2335

Gly Gly Glu Pro Ser Pro Glu Gly Thr Thr Gly Gln Ser Tyr Asn Gln
        2340                2345                2350

Tyr Ser Gln Arg Tyr His Gln Arg Thr Asn Thr Asn Val Asn Cys Pro
    2355                2360                2365

Ile Glu Cys Phe Met Pro Leu Asp Val Gln Ala Asp Arg Glu Asp Ser
2370                2375                2380

Arg Glu
385

(2) INFORMATION FOR SEQ ID NO:13:

(i) SEQUENCE CHARACTERISTICS:
        (A) LENGTH: 3757 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GACGACCACT GCCAGGGACG AAAGTGCAAT GCGGCATACC TCAGTGGCGT GGAGTGCAGG      60

TATACAGATT AATCCGGCAG CGTCCGTCGT TGTTGATATT GCTTATGAAG GCTCCGGCAG     120

TGGCGACTGG CGTACTGACG GATTCATCGT TGGGGTCGGT TATAAATTCT GATTAGCCAG     180

GTAACACAGT GTTATGACAG CCCGCCGGAA CCGGTGGGCT TTTTTGTGGG GTGAATATGG     240

CAGTAAAGAT TTCAGGAGTC CTGAAAGACG GCACAGGAAA ACCGGTACAG AACTGCACCA     300

TTCAGCTGAA AGCCAGACGT AACAGCACCA CGGTGGTGGT GAACACGGTG GGCTCAGAGA     360

ATCCGGATGA AGCCTGCTTT TTTATACTAA GTTGGCATTA TAAAAAGCA TTGCTTATCA      420

ATTTGTTGCA ACGAACAGGT CACTATCAGT CAAAATAAAA TCATTATTTG ATTTCAATTT     480

TGTCCCACTC CCTGCCTCTG TCATCACGAT ACTGTGATGC CATGGTGTCC GACTTATGCC     540

CGAGAAGATG TTGAGCAAAC TTATCGCTTA TCTGCTTCTC ATAGAGTCTT GCAGACAAAC     600
```

```
TGCGCAACTC GTGAAAGGTA GGCGGATCTG GGTCGACCTG CAGGTCAACG GATCCTCTCC    660

AGTGGAAAGC TGAGCCCAAC CCTGAGGACT CAGAGGATGC AAGATGAACG ACGCTGTTAC    720

CCATTGTGCT CTGCTCCTTG GGATGGCTCA CAGACACCAT CATCTCCTGT CCTGTCTCAC    780

TCTTGGGAAA TGTGTTAGAG TGTGTCAATA TGTCATGCTA GGGTGACACT GAGCCAGGAG    840

CCTTCTTGAG ACCTCTATAT CCCTGGGATG GGATCCCCAT CCCAATAGTT GGAAGGAGCA    900

GCGGCTCGGT GATGCAGAGC ACTCAACTGA GAGGCATCCT CAGTATGCGG TGCTCTGCCC    960

ACAGTGGACA GAGCAGACCT GGTGGAGGCA GAGCAGAGTA ACATCCTGAG CAGATGGGGG    1020

CCACGCCTGC CCAGGTCTCC TGATGTGGAG GGCTGCTTGT GGGACATCTG GCAAGCTCAG    1080

CATTTCCTTG GGCATTTCAC CGCTGAGGAA CAAGACATGA GGAGGAGGCA AATCTGAGAA    1140

GAGGCTACCA GCCTCCCCTC AGAAGATACC CCTTTCCAGG GAGGGCTGGG GATGACCACT    1200

GTCCTGCCAG CCCATCCACC CCACTACCTG ACTCTCCTAT CCTGGACCCA GAGCAGTTGC    1260

ATCTCTTAAC TCTGCCTTCC ATAGCCTGAA ATACCAAGAC TCTGTGTGTG TGTGTGTGTG    1320

TGTGTGTGTG TGTGTGTGTG TGTGTGTGTG TGTATGTGTA TGTGTGTGTG TATGACTGGT    1380

CCTCTCATTG TGCACTCAAC CGTGTGACCT GTGGTCATCA GAAGGGCATC TGGGTGGTGG    1440

GGACACATGT TACATGGAGG CCTTTGATCT AAATCACTAT TTCCTTTGTA TCTGGATTGG    1500

CGGGTGCTGT GTCCCTCCTC TCATGCACTC TGGTCTGGAG AATTAAAAAG GCAGAGGACA    1560

GCAGGCCAAG GAGAGAGGAG CAGAGACAGC TAAGGTAAAG TCCTGGTGTC TATATGTCAT    1620

CCTGAAGCAG AGTAACCAAG CTTGTGACCT TTGTAACCTG GTGCACCAAG CCCGCAGACT    1680

CCTGGGATGA ACCTGCCCTC CATCTCATGG GCCCTGGTTC CATTCTGGAC TTGATATTCT    1740

GCCAGCCCCA GTCCAGCCCT GTCTTCTAGC TGGACTCAGG CTGTGCTCCT CTCTGCTTCC    1800

AGATGCTGAA GCGGCGGCTG CTGCTGCTGT GGGCACTGTC CCTCCTGGCT AGTCTGGTGT    1860

ACTCAGCCCC TCGTAAGTTG TCTTGAGCCC TCCCTGTCTC TCCCTCACCT TCACAGGCCA    1920

CAGGAATGGG GAGTCTAGAG AATCCCAGGG TTAGCTCCAA TTCAGGAGGG GGCAAGGCAG    1980

GGCACAGAGG TTGCTTCTTG TCTCTCTCCA GGCCCAGCCA ATCAGCGAGT GGGCATCGTG    2040

GGAGGACATG AGGCTTCTGA GAGTAAGTGG CCCTGGCAGG TGAGCCTGAG ATTTAAATTA    2100

AACTACTGGA TACATTTCTG CGGAGGCTCT CTCATCCACC CACAGTGGGT GCTCACTGCG    2160

GCACACTGTG TGGGACCGTG AGTCTCCCTG GGCCTGGCAT GGTGGGACGG GATCTAGATT    2220

ATTCCCACCA TCCCCAGTGT TCCCGAGGAT GTGCCCATCC TGGCTGGAGC CTTCTGAGCA    2280

TGATTATACT CTTCTAGGCA CATCAAAAGC CCACAGCTCT TCCGGGTGCA GCTTCGTGAG    2340

CAGTATCTAT ACTATGGGGA CCAGCTCCTC TCTTTGAACC GGATCGTGGT GCACCCCCAC    2400

TATTACACGG CCGAGGGTGG GGCAGACGTT GCCCTGCTGG AGCTTGAGGT CCCTGTGAAT    2460

GTCTCCACCC ATATCCACCC CATATCCCTG CCCCCTGCCT CGGAGACCTT CCCCCCTGGG    2520

ACATCGTGCT GGGTGACAGG CTGGGCGAC ATTGATAATG ACGGTATGTG GCAAGGATAG    2580

CTGACAGTTA GGCAGGGACT AAGTCTCCTC CAATCCCAGC ATTGGAGGGT GGGCAGGGAT    2640

TCCAGTGGCT GGTTACTCTT GAGCCTCCCT CAAAGGCTGC ACTTGTCCCA CCCCAGAGCC    2700

TCTCCCACCT CCTTATCCTC TGAAGCAAGT GAAGGTTCCC ATTGTGGAAA ACAGCCTGTG    2760

TGACCGGAAG TACCACACTG GCCTCTACAC GGGAGATGAT TTTCCCATTG TCCATGATGG    2820

CATGCTGTGT GCTGGAAATA CCAGGAGAGA CTCCTGCCAG GTAGGTCCTG TGTCCTCCCT    2880

GCACCACACC CCATCTGGTC TCCATACTGT GTGCTGACCC CTGTCTTCTT CAGGGCGATT    2940

CAGGGGGGCC ACTGGTCTGC AAAGTGAAGG GTACCTGGCT GCAGGCAGGA GTGGTCAGCT    3000
```

```
GGGGTGAGGG CTGCGCACAG CCCAACAAGC CTGGCATCTA CACCCGGGTG ACATACTACT    3060

TAGACTGGAT CCACCGCTAT GTCCCTGAGC ATTCCTGAGA CCTATCCAGG GTCAGGCAAG    3120

AACCAGGGCC GTGCTGTCTT TAACTCACTG CTTCCTGGTC AGGTGGAACC CTTGCCTTCC    3180

TTGTCCTCTG TCTCCCCTGT CTACTAGGTG TCCCTCTGAG GCCCCCACCC CCCAGTTCCG    3240

TCTTGAGTCC CTAGCCATTC CGGTTCCCTC TTGCCTCCCA CCACATAATA GTTGCATTGT    3300

GTGGCTCCCT CTCTTCTGTG GCTCATTAAA GTACTTGAAA ACAGCTATTG GAGTTGCTTC    3360

AAGAGTTCAA GGTCATCCTT GTCTATGTAT TGAGGTCGAG GCCAGTCTGG GATATGTGAG    3420

GCACCATCCC AAGACCATAA AGATCAAAAA TAAGTTCATG CAGCGGCACA TTTGCCTGCT    3480

ACAGTACACA ACATCACATC TGGCTGCTCC AGTCATGCAG TGGTACATCT GGCTGCTCCA    3540

GTCACATAGG AGCACATCTG GCTGCTCCAG TCATGCAGTG GTACATCTGG CTGCTCCAGT    3600

CACATAGGAG CACATCTGGC TGCTCCAGTC ACTTTGCTTT GGGTATTCTC ATTTGAGCCT    3660

CTTGGCCCTT GGGTGCTCAT GGCCATTCCT GCACACACAC ATATGCTTAT ATCTGGAACT    3720

TTCTGCTGAA GGGAGCTGTT GGTTCATGAA TAGGCCC                            3757

(2) INFORMATION FOR SEQ ID NO:14:

(i) SEQUENCE CHARACTERISTICS:
        (A) LENGTH: 1108 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

ATCCAATTGA AGAGAGGAGC AGAGACAGCT AAGATGCTGA AGCGGCGGCT GCTGCTGCTG     60

TGGGCACTGT CCCTCCTGGC TAGTCTGGTG TACTCAGCCC CTCGCCCAGC CAATCAGCGA    120

GTGGGCATCG TGGGAGGACA TGAGGCTTCT GAGAGTAAGT GGCCCTGGCA GGTGAGCCTG    180

AGATTTAAAT TAAACTACTG GATACATTTC TGCGGAGGCT CTCTCATCCA CCCACAGTGG    240

GTGCTCACTG CGGCACACTG TGTGGGACCG CACATCAAAA GCCCACAGCT CTTCCGGGTG    300

CAGCTTCGTG AGCAGTATCT ATACTATGGG GACCAGCTCC TCTCTTTGAA CCGGATCGTG    360

GTGCACCCCC ACTATTACAC GGCCGAGGGT GGGGCAGACG TTGCCCTGCT GGAGCTTGAG    420

GTCCCTGTGA ATGTCTCCAC CCATATCCAC CCCATATCCC TGCCCCCTGC CTCGGAGACC    480

TTCCCCCCTG GGACATCGTG CTGGGTGACA GGCTGGGGCG ACATTGATAA TGACGAGCCT    540

CTCCCACCTC CTTATCCTCT GAAGCAAGTG AAGGTTCCCA TTGTGGAAAA CAGCCTGTGT    600

GACCGGAAGT ACCACACTGG CCTCTACACG GGAGATGATT TTCCCATTGT CCATGATGGC    660

ATGCTGTGTG CTGGAAATAC CAGGAGAGAC TCCTGCCAGG GCGATTCAGG GGGGCCACTG    720

GTCTGCAAAG TGAAGGGTAC CTGGCTGCAG GCAGGAGTGG TCAGCTGGGG TGAGGGCTGC    780

GCACAGCCCA ACAAGCCTGG CATCTACACC CGGGTGACAT ACTACTTAGA CTGGATCCAC    840

CGCTATGTCC CTGAGCATTC CTGAGACCTA TCCAGGGTCA GGCAAGAACC AGGGCCGTGC    900

TGTCTTTAAC TCACTGCTTC CTGGTCAGGT GGAACCCTTG CCTTCCTTGT CCTCTGTCTC    960

CCCTGTCTAC TAGGTGTCCC TCTGAGGCCC CCACCCCCA GTTCCGTCTT GAGTCCCTAG    1020

CCATTCCGGT TCCCTCTTGC CTCCCACCAC ATAATAGTTG CATTGTGTGG CTCCCTCTCT   1080

TCTGTGGCTC ATTAAAGTAC TTGAAAAC                                    1108

(2) INFORMATION FOR SEQ ID NO:15:
```

(i) SEQUENCE CHARACTERISTICS:
    (A) LENGTH: 276 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:15:

Met Leu Lys Arg Arg Leu Leu Leu Trp Ala Leu Ser Leu Leu Ala
1               5                   10                  15

Ser Leu Val Tyr Ser Ala Pro Arg Pro Ala Asn Gln Arg Val Gly Ile
            20                  25                  30

Val Gly Gly His Glu Ala Ser Glu Ser Lys Trp Pro Trp Gln Val Ser
        35                  40                  45

Leu Arg Phe Lys Leu Asn Tyr Trp Ile His Phe Cys Gly Gly Ser Leu
    50                  55                  60

Ile His Pro Gln Trp Val Leu Thr Ala Ala His Cys Val Gly Pro His
65                  70                  75                  80

Ile Lys Ser Pro Gln Leu Phe Arg Val Gln Leu Arg Glu Gln Tyr Leu
                85                  90                  95

Tyr Tyr Gly Asp Gln Leu Leu Ser Leu Asn Arg Ile Val Val His Pro
            100                 105                 110

His Tyr Tyr Thr Ala Glu Gly Gly Ala Asp Val Ala Leu Leu Glu Leu
        115                 120                 125

Glu Val Pro Val Asn Val Ser Thr His Ile His Pro Ile Ser Leu Pro
130                 135                 140

Pro Ala Ser Glu Thr Phe Pro Pro Gly Thr Ser Cys Trp Val Thr Gly
145                 150                 155                 160

Trp Gly Asp Ile Asp Asn Asp Glu Pro Leu Pro Pro Tyr Pro Leu
                165                 170                 175

Lys Gln Val Lys Val Pro Ile Val Glu Asn Ser Leu Cys Asp Arg Lys
            180                 185                 190

Tyr His Thr Gly Leu Tyr Thr Gly Asp Asp Phe Pro Ile Val His Asp
        195                 200                 205

Gly Met Leu Cys Ala Gly Asn Thr Arg Arg Asp Ser Cys Gln Gly Asp
210                 215                 220

Ser Gly Gly Pro Leu Val Cys Lys Val Lys Gly Thr Trp Leu Gln Ala
225                 230                 235                 240

Gly Val Val Ser Trp Gly Glu Gly Cys Ala Gln Pro Asn Lys Pro Gly
                245                 250                 255

Ile Tyr Thr Arg Val Thr Tyr Tyr Leu Asp Trp Ile His Arg Tyr Val
            260                 265                 270

Pro Glu His Ser
        275

(2) INFORMATION FOR SEQ ID NO:16:

(i) SEQUENCE CHARACTERISTICS:
        (A) LENGTH: 1154 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GGAATTCCGT GGCCAGGATG CTGAGCCTGC TGCTGCTGGC GCTGCCCGTC CTGGCGAGCC    60

-continued

```
GCGCCTACGC GGCCCCTGCC CCAGTCCAGG CCCTGCAGCA AGCGGGTATC GTCGGGGGTC      120
AGGAGGCCCC CAGGAGCAAG TGGCCCTGGC AGGTGAGCCT GAGAGTCCGC GACCGATACT      180
GGATGCACTT CTGCGGGGGC TCCCTCATCC ACCCCCAGTG GGTGCTGACC GCGGCGCACT      240
GCCTGGGACC GGACGTCAAG GATCTGGCCA CCCTCAGGGT GCAACTGCGG GAGCAGCACC      300
TCTACTACCA GGACCAGCTG CTGCCAGTCA GCAGGATCAT CGTGCACCCA CAGTTCTACA      360
TCATCCAGAC TGGAGCGGAT ATCGCCCTGC TGGAGCTGGA GGAGCCCGTG AACATCTCCA      420
GCCGCGTCCA CACGGTCATG CTGCCCCCTG CCTCGGAGAC CTTCCCCCCG GGGATGCCGT      480
GCTGGGTCAC TGGCTGGGGC GATGTGGACA ATGATGAGCC CCTCCCACCG CCATTTCCCC      540
TGAAGCAGGT GAAGGTCCCC ATAATGGAAA ACCACATTTG TGACGCAAAA TACCACCTTG      600
GCGCCTACAC GGGAGACGAC GTCCGCATCA TCCGTGACGA CATGCTGTGT GCCGGGAACA      660
GCCAGAGGGA CTCCTGCAAG GGCGACTCTG GAGGGCCCCT GGTGTGCAAG GTGAATGGCA      720
CCTGGCTACA GGCGGGCGTG GTCAGCTGGG ACGAGGGCTG TGCCCAGCCC AACCGGCCTG      780
GCATCTACAC CCGTGTCACC TACTACTTGG ACTGGATCCA CCACTATGTC CCCAAAAAGC      840
CGTGAGTCAG GCCTGGGTGT GCCACCTGGG TCACTGGAGG ACCAACCCCT GCTGTCCAAA      900
ACACCACTGC TTCCTACCCA GGTGGCGACT GCCCCCCACA CCTTCCCTGC CCCGTCCTGA      960
GTGCCCCTTC CTGTCCTAAG CCCCCTGCTC TCTTCTGAGC CCCTTCCCCT GTCCTGAGGA     1020
CCCTTCCCCA TCCTGAGCCC CCTTCCCTGT CCTAAGCCTG ACGCCTGCAC TGCTCCGGCC     1080
CTCCCCTGCC CAGGCAGCTG GTGGTGGGCG CTAATCCTCC TGAGTGCTGG ACCTCATTAA     1140
AGTGCATGGA AATC                                                       1154
```

(2) INFORMATION FOR SEQ ID NO:17:

(i) SEQUENCE CHARACTERISTICS:
        (A) LENGTH: 275 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

```
Met Leu Ser Leu Leu Leu Ala Leu Pro Val Leu Ala Ser Arg Ala
 1               5                  10                  15

Tyr Ala Ala Pro Ala Pro Val Gln Ala Leu Gln Gln Ala Gly Ile Val
                20                  25                  30

Gly Gly Gln Glu Ala Pro Arg Ser Lys Trp Pro Trp Gln Val Ser Leu
            35                  40                  45

Arg Val Arg Asp Arg Tyr Trp Met His Phe Cys Gly Gly Ser Leu Ile
50                  55                  60

His Pro Gln Trp Val Leu Thr Ala Ala His Cys Leu Gly Pro Asp Val
65                  70                  75                  80

Lys Asp Leu Ala Thr Leu Arg Val Gln Leu Arg Glu Gln His Leu Tyr
                85                  90                  95

Tyr Gln Asp Gln Leu Leu Pro Val Ser Arg Ile Ile Val His Pro Gln
                100                 105                 110

Phe Tyr Ile Ile Gln Thr Gly Ala Asp Ile Ala Leu Leu Glu Leu Glu
            115                 120                 125

Glu Pro Val Asn Ile Ser Ser Arg Val His Thr Val Met Leu Pro Pro
            130                 135                 140

Ala Ser Glu Thr Phe Pro Pro Gly Met Pro Cys Trp Val Thr Gly Trp
145                 150                 155                 160
```

```
Gly Asp Val Asp Asn Asp Glu Pro Leu Pro Pro Phe Pro Leu Lys
                165                 170                 175

Gln Val Lys Val Pro Ile Met Glu Asn His Ile Cys Asp Ala Lys Tyr
            180                 185                 190

His Leu Gly Ala Tyr Thr Gly Asp Asp Val Arg Ile Ile Arg Asp Asp
            195                 200                 205

Met Leu Cys Ala Gly Asn Ser Gln Arg Asp Ser Cys Lys Gly Asp Ser
210                 215                 220

Gly Gly Pro Leu Val Cys Lys Val Asn Gly Thr Trp Leu Gln Ala Gly
225                 230                 235                 240

Val Val Ser Trp Asp Glu Gly Cys Ala Gln Pro Asn Arg Pro Gly Ile
                245                 250                 255

Tyr Thr Arg Val Thr Tyr Tyr Leu Asp Trp Ile His His Tyr Val Pro
                260                 265                 270

Lys Lys Pro
        275
```

(2) INFORMATION FOR SEQ ID NO:18:

(i) SEQUENCE CHARACTERISTICS:
        (A) LENGTH: 1137 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
TGAATCTGCT GCTGCTGGCG CTGCCCGTCC TGGCGAGCCG CGCCTACGCG GCCCCTGCCC    60
CAGGCCAGGC CCTGCAGCGA GTGGGCATCG TCGGGGGTCA GGAGGCCCCC AGGAGCAAGT   120
GGCCCTGGCA GGTGAGCCTG AGAGTCCACG GCCCATACTG GATGCACTTC TGCGGGGGCT   180
CCCTCATCCA CCCCCAGTGG GTGCTGACCG CAGCGCACTG CGTGGGACCG GACGTCAAGG   240
ATCTGGCCGC CCTCAGGGTG CAACTGCGGG AGCAGCACCT CTACTACCAG GACCAGCTGC   300
TGCCGGTCAG CAGGATCATC GTGCACCCAC AGTTCTACAC CGCCCAGATC GGAGCGGACA   360
TCGCCCTGCT GGAGCTGGAG GAGCCGGTGA ACGTCTCCAG CCACGTCCAC ACGGTCACCC   420
TGCCCCCTGC CTCAGAGACC TTCCCCCCGG GGATGCCGTG CTGGGTCACT GGCTGGGGCG   480
ATGTGGACAA TGATGAGCGC CTCCCACCGC CATTTCCTCT GAAGCAGGTG AAGGTCCCCA   540
TAATGGAAAA CCACATTTGT GACGCAAAAT ACCACCTTGG CGCCTACACG GGAGACGACG   600
TCCGCATCGT CCGTGACGAC ATGCTGTGTG CCGGGAACAC CCGGAGGGAC TCATGCCAGG   660
GCGACTCCGG AGGGCCCCTG GTGTGCAAGG TGAATGGCAC CTGGCTGCAG GCGGGCGTGG   720
TCAGCTGGGG CGAGGGCTGT GCCCAGCCCA ACCGGCCTGG CATCTACACC CGTGTCACCT   780
ACTACTTGGA CTGGATCCAC CACTATGTCC CCAAAAAGCC GTGAGTCAGG CCTGGGTTGG   840
CCACCTGGGT CACTGGAGGA CCAACCCCTG CTGTCCAAAA CACCACTGCT TCCTACCCAG   900
GTGGCGACTG CCCCCCACAC CTTCCCTGCC CCGTCCTGAG TGCCCCTTCC TGTCCTAAGC   960
CCCCTGCTCT CTTCTGAGCC CCTTCCCCTG TCCTGAGGAC CCTTCCCTAT CCTGAGCCCC  1020
CTTCCCTGTC CTAAGCCTGA CGCCTGCACC GGGCCCTCCA GCCCTCCCCT GCCCAGATAG  1080
CTGGTGGTGG GCGCTAATCC TCCTGAGTGC TGGACCTCAT TAAAGTGCAT GGAAATC     1137
```

(2) INFORMATION FOR SEQ ID NO:19:

(i) SEQUENCE CHARACTERISTICS:

(A) LENGTH: 273 amino acids
(B) TYPE: amino acid
(C) STRANDEDNESS: single
(D) TOPOLOGY: linear (xi) SEQUENCE DESCRIPTION: SEQ ID NO:19:

```
Asn Leu Leu Leu Ala Leu Pro Val Leu Ala Ser Arg Ala Tyr Ala
 1               5                  10                  15

Ala Pro Ala Pro Gly Gln Ala Leu Gln Arg Val Gly Ile Val Gly Gly
            20                  25                  30

Gln Glu Ala Pro Arg Ser Lys Trp Pro Trp Gln Val Ser Leu Arg Val
        35                  40                  45

His Gly Pro Tyr Trp Met His Phe Cys Gly Gly Ser Leu Ile His Pro
    50                  55                  60

Gln Trp Val Leu Thr Ala Ala His Cys Val Gly Pro Asp Val Lys Asp
65                  70                  75                  80

Leu Ala Ala Leu Arg Val Gln Leu Arg Glu Gln His Leu Tyr Tyr Gln
                85                  90                  95

Asp Gln Leu Leu Pro Val Ser Arg Ile Ile Val His Pro Gln Phe Tyr
            100                 105                 110

Thr Ala Gln Ile Gly Ala Asp Ile Ala Leu Leu Glu Leu Glu Glu Pro
        115                 120                 125

Val Asn Val Ser Ser His Val His Thr Val Thr Leu Pro Pro Ala Ser
130                 135                 140

Glu Thr Phe Pro Pro Gly Met Pro Cys Trp Val Thr Gly Trp Gly Asp
145                 150                 155                 160

Val Asp Asn Asp Glu Arg Leu Pro Pro Pro Phe Pro Leu Lys Gln Val
                165                 170                 175

Lys Val Pro Ile Met Glu Asn His Ile Cys Asp Ala Lys Tyr His Leu
            180                 185                 190

Gly Ala Tyr Thr Gly Asp Asp Val Arg Ile Val Arg Asp Asp Met Leu
        195                 200                 205

Cys Ala Gly Asn Thr Arg Arg Asp Ser Cys Gln Gly Asp Ser Gly Gly
    210                 215                 220

Pro Leu Val Cys Lys Val Asn Gly Thr Trp Leu Gln Ala Gly Val Val
225                 230                 235                 240

Ser Trp Gly Glu Gly Cys Ala Gln Pro Asn Arg Pro Gly Ile Tyr Thr
                245                 250                 255

Arg Val Thr Tyr Tyr Leu Asp Trp Ile His His Tyr Val Pro Lys Lys
            260                 265                 270

Pro
```

(2) INFORMATION FOR SEQ ID NO:20:

(i) SEQUENCE CHARACTERISTICS:
(A) LENGTH: 1128 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:20:

```
GCTGAATCTG CTGCTGCTGG CGCTGCCCGT CCTGGCGAGC CGCGCCTACG CGGCCCCTGC      60

CCCAGGCCAG GCCCTGCAGC GAGTGGGCAT CGTTGGGGGT CAGGAGGCCC CCAGGAGCAA     120

GTGGCCCTGG CAGGTGAGCC TGAGAGTCCA CGGCCCATAC TGGATGCACT TCTGCGGGGG     180

CTCCCTCATC CACCCCCAGT GGGTGCTGAC CGCAGCGCAC TGCGTGGGAC CGGACGTCAA     240
```

```
GGATCTGGCC GCCCTCAGGG TGCAACTGCG GGAGCAGCAC CTCTACTACC AGGACCAGCT    300

GCTGCCGGTC AGCAGGATCA TCGTGCACCC ACAGTTCTAC ACCGCCCAGA TCGGAGCGGA    360

CATCGCCCTG CTGGAGCTGG AGGAGCCGGT GAAGGTCTCC AGCCACGTCC ACACGGTCAC    420

CCTGCCCCCT GCCTCAGAGA CCTTCCCCCC GGGGATGCCG TGCTGGGTCA CTGGCTGGGG    480

CGATGTGGAC AATGATGAGC GCCTCCCACC GCCATTTCCT CTGAAGCAGG TGAAGGTCCC    540

CATAATGGAA AACCACATTT GTGACGCAAA ATACCACCTT GGCGCCTACA CGGGAGACGA    600

CGTCCGCATC GTCCGTGACG ACATGCTGTG TGCCGGGAAC ACCCGGAGGG ACTCATGCCA    660

GGGCGACTCC GGAGGGCCCC TGGTGTGCAA GGTGAATGGC ACCTGGCTGC AGGCGGGCGT    720

GGTCAGCTGG GGCGAGGGCT GTGCCCAGCC CAACCGGCCT GGCATCTACA CCCGTGTCAC    780

CTACTACTTG GACTGGATCC ACCACTATGT CCCCAAAAAG CCGTGAGTCA GGCCTGGGTT    840

GGCCACCTGG GTCACTGGAG GACCAACCCC TGCTGTCCAA AACACCACTG CTTCCTACCC    900

AGGTGGCGAC TGCCCCCCAC ACCTTCCCTG CCCCGTCCTG AGTGCCCCTT CCTGTCCTAA    960

GCCCCCTGCT CTCTTCTGAG CCCCTTCCCC TGTCCTGAGG ACCCTTCCCC ATCCTGAGCC   1020

CCCTTCCCTG TCCTAAGCCT GACGCCTGCA CCGGGCCCTC CGGCCCTCCC CTGCCCAGGC   1080

AGCTGGTGGT GGGCGCTAAT CCTCCTGAGT GCTGGACCTC ATTAAAGT               1128
```

(2) INFORMATION FOR SEQ ID NO:21:

(i) SEQUENCE CHARACTERISTICS:
        (A) LENGTH: 274 amino acids
        (B) TYPE: amino acid
        (C) STRANDEDNESS: single
        (D) TOPOLOGY: linear (xi) SEQUENCE DESCRIPTION: SEQ ID NO:21:

```
Leu Asn Leu Leu Leu Leu Ala Leu Pro Val Leu Ala Ser Arg Ala Tyr
  1               5                  10                  15

Ala Ala Pro Ala Pro Gly Gln Ala Leu Gln Arg Val Gly Ile Val Gly
             20                  25                  30

Gly Gln Glu Ala Pro Arg Ser Lys Trp Pro Trp Gln Val Ser Leu Arg
         35                  40                  45

Val His Gly Pro Tyr Trp Met His Phe Cys Gly Gly Ser Leu Ile His
     50                  55                  60

Pro Gln Trp Val Leu Thr Ala Ala His Cys Val Gly Pro Asp Val Lys
 65                  70                  75                  80

Asp Leu Ala Ala Leu Arg Val Gln Leu Arg Glu Gln His Leu Tyr Tyr
                 85                  90                  95

Gln Asp Gln Leu Leu Pro Val Ser Arg Ile Ile Val His Pro Gln Phe
            100                 105                 110

Tyr Thr Ala Gln Ile Gly Ala Asp Ile Ala Leu Leu Glu Leu Glu Glu
        115                 120                 125

Pro Val Lys Val Ser Ser His Val His Thr Val Thr Leu Pro Pro Ala
    130                 135                 140

Ser Glu Thr Phe Pro Pro Gly Met Pro Cys Trp Val Thr Gly Trp Gly
145                 150                 155                 160

Asp Val Asp Asn Asp Glu Arg Leu Pro Pro Pro Phe Pro Leu Lys Gln
                165                 170                 175

Val Lys Val Pro Ile Met Glu Asn His Ile Cys Asp Ala Lys Tyr His
            180                 185                 190

Leu Gly Ala Tyr Thr Gly Asp Asp Val Arg Ile Val Arg Asp Asp Met
        195                 200                 205
```

```
Leu Cys Ala Gly Asn Thr Arg Arg Asp Ser Cys Gln Gly Asp Ser Gly
    210                 215                 220

Gly Pro Leu Val Cys Lys Val Asn Gly Thr Trp Leu Gln Ala Gly Val
225                 230                 235                 240

Val Ser Trp Gly Glu Gly Cys Ala Gln Pro Asn Arg Pro Gly Ile Tyr
                245                 250                 255

Thr Arg Val Thr Tyr Tyr Leu Asp Trp Ile His His Tyr Val Pro Lys
            260                 265                 270

Lys Pro
```

(2) INFORMATION FOR SEQ ID NO:22:

(i) SEQUENCE CHARACTERISTICS:
        (A) LENGTH: 1081 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

```
GCTGCCCGTC CTGGCGAGCC GCGCCTACGC GGCCCCTGCC CCAGGCCAGG CCCTGCAGCG      60
AGTGGGCATC GTTGGGGGTC AGGAGGCCCC CAGGAGCAAG TGGCCCTGGC AGGTGAGCCT     120
GAGAGTCCGC GACCGATACT GGATGCACTT CTGCGGGGGC TCCCTCATCC ACCCCCAGTG     180
GGTGCTGACC GCAGCGCACT GCGTGGGACC GGACGTCAAG GATCTGGCCG CCCTCAGGGT     240
GCAACTGCGG GAGCAGCACC TCTACTACCA GGACCAGCTG CTGCCGGTCA GCAGGATCAT     300
CGTGCACCCA CAGTTCTACA CCGCCCAGAT CGGAGCGGAC ATCGCCCTGC TGGAGCTGGA     360
GGAGCCGGTG AAGGTCTCCA GCCACGTCCA CACGGTCACC CTGCCCCCTG CCTCAGAGAC     420
CTTCCCCCCG GGGATGCCGT GCTGGGTCAC TGGCTGGGGC GATGTGGACA ATGATGAGCG     480
CCTCCCACCG CCATTTCCTC TGAAGCAGGT GAAGGTCCCC ATAATGGAAA ACCACATTTG     540
TGACGCAAAA TACCACCTTG GCGCCTACAC GGGAGACGAC GTCCGCATCG TCCGTGACGA     600
CATGCTGTGT GCCGGGAACA CCCGGAGGGA CTCATGCCAG GGCGACTCCG GAGGGCCCCT     660
GGTGTGCAAG GTGAATGGCA CCTGGCTGCA GGCGGGCGTG GTCAGCTGGG GCGAGGGCTG     720
TGCCCAGCCC AACCGGCCTG GCATCTACAC CCGTGTCACC TACTACTTGG ACTGGATCCA     780
CCACTATGTC CCCAAAAAGC CGTGAGTCAG GCCTGGGGTG TCCACCTGGG TCACTGGAGG     840
ACCAGCCCCT CCTGTCCAAA ACACCACTGC TTCCTACCCA GGCGGCGACT GCCCCCCACA     900
CCTTCCCTGC CCCGTCCTGA GTGCCCCTTC CTGTCCTAAG CCCCCTGCTC TCTTCTGAGC     960
CCCTTCCCCT GTCCTGAGGA CCCTTCCCCA TCCTGAGCCC CCTTCCCTGT CCTAAGCCTG    1020
ACGCCTGCAC CGGGCCCTCC GGCCCTCCCC TGCCCAGGCA GCTGGTGGTG GGCGCTAATC    1080
C                                                                    1081
```

(2) INFORMATION FOR SEQ ID NO:23:

(i) SEQUENCE CHARACTERISTICS:
        (A) LENGTH: 267 amino acids
        (B) TYPE: amino acid
        (C) STRANDEDNESS: single
        (D) TOPOLOGY: linear (xi) SEQUENCE DESCRIPTION: SEQ ID NO:23:

```
Leu Pro Val Leu Ala Ser Arg Ala Tyr Ala Ala Pro Ala Pro Gly Gln
1               5                  10                  15
```

```
Ala Leu Gln Arg Val Gly Ile Val Gly Gln Glu Ala Pro Arg Ser
            20                  25                  30

Lys Trp Pro Trp Gln Val Ser Leu Arg Val Arg Asp Arg Tyr Trp Met
        35                  40                  45

His Phe Cys Gly Gly Ser Leu Ile His Pro Gln Trp Val Leu Thr Ala
 50                  55                  60

Ala His Cys Val Gly Pro Asp Val Lys Asp Leu Ala Ala Leu Arg Val
 65                  70                  75                  80

Gln Leu Arg Glu Gln His Leu Tyr Tyr Gln Asp Gln Leu Leu Pro Val
                85                  90                  95

Ser Arg Ile Ile Val His Pro Gln Phe Tyr Thr Ala Gln Ile Gly Ala
            100                 105                 110

Asp Ile Ala Leu Leu Glu Leu Glu Glu Pro Val Lys Val Ser Ser His
        115                 120                 125

Val His Thr Val Thr Leu Pro Pro Ala Ser Glu Thr Phe Pro Pro Gly
    130                 135                 140

Met Pro Cys Trp Val Thr Gly Trp Gly Asp Val Asp Asn Asp Glu Arg
145                 150                 155                 160

Leu Pro Pro Pro Phe Pro Leu Lys Gln Val Lys Val Pro Ile Met Glu
                165                 170                 175

Asn His Ile Cys Asp Ala Lys Tyr His Leu Gly Ala Tyr Thr Gly Asp
            180                 185                 190

Asp Val Arg Ile Val Arg Asp Asp Met Leu Cys Ala Gly Asn Thr Arg
        195                 200                 205

Arg Asp Ser Cys Gln Gly Asp Ser Gly Gly Pro Leu Val Cys Lys Val
    210                 215                 220

Asn Gly Thr Trp Leu Gln Ala Gly Val Val Ser Trp Gly Glu Gly Cys
225                 230                 235                 240

Ala Gln Pro Asn Arg Pro Gly Ile Tyr Thr Arg Val Thr Tyr Tyr Leu
                245                 250                 255

Asp Trp Ile His His Tyr Val Pro Lys Lys Pro
            260                 265
```

(2) INFORMATION FOR SEQ ID NO:24:

(i) SEQUENCE CHARACTERISTICS:
        (A) LENGTH: 1103 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

```
TGCCGAGACA GCCAAGATGC TGAAGCTGCT GCTGCTGCTG GCACTGTCCC CCCTGGCTAG    60

TCTGGTGCAC GCGGCCCCTT GCCCAGTCAA GCAGCGAGTG GGCATTGTGG GAGGACGAGA   120

GGCTTCTGAA AGTAAGTGGC CCTGGCAGGT GAGCCTGAGA TTTAAATTCA GCTTCTGGAT   180

GCATTTCTGT GGCGGCTCCC TCATTCACCC ACAGTGGGTG CTCACTGCGG CACACTGTGT   240

GGGACTGCAC ATCAAAAGCC CAGAGCTCTT CCGTGTACAG CTTCGTGAGC AGTATCTATA   300

CTATGCGGAC CAGCTACTGA CTGTGAACCG GACCGTTGTG CACCCCCACT ACTACACAGT   360

CGAGGATGGG GCAGACATTG CCCTGCTGGA GCTTGAGAAC CCTGTGAATG TCTCCACCCA   420

TATCCACCCC ACATCCCTGC CCCCTGCCTC GGAGACCTTC CCCTCGGGGA CTTCTTGCTG   480

GGTAACAGGC TGGGGCGACA TTGATAGTGA CGAGCCTCTC CTGCCACCTT ATCCTCTGAA   540

GCAAGTGAAG GTCCCCATTG TGGAAAACAG CCTGTGTGAT CGGAAGTACC ACACTGGCCT   600
```

-continued

```
CTACACAGGA GATGATGTTC CCATTGTCCA GGATGGCATG CTGTGTGCTG GAAATACCAG    660

GAGCGACTCC TGCCAGGGAG ACTCAGGGGG CCCACTGGTC TGCAAAGTGA AGGGTACCTG    720

GCTGCAAGCA GGAGTGGTCA GCTGGGGCGA GGGCTGCGCA GAGGCCAATC GTCCTGGCAT    780

TTACACCCGG GTGACGTACT ACCTGGACTG GATTCACCGC TATGTCCCTC AGCGTTCCTG    840

AGACCCATCC AGGGTCAGGG AAGAACCAGG CACCTGCTGT CTTTAACTCA CTGCTTCCTG    900

GCCAGATGGA ACCCTGGCCT TCTTTGTACT CTGTCTCCCC TGTCTTCCGG GTGTCCCTCT    960

GAGCCCCCAC TTTGTTCCAC CTTGAGTCCC TCGCCACTCC TGTCCCCTCT GCCTCCCACC   1020

ACACACAGCT GCACTGTGCG GCTCCCTCTT TTCTGTGGCT CATTAAAGTA TGTGAAAATT   1080

TTGCTCCAAA AAAAAAAAAA AAA                                          1103
```

(2) INFORMATION FOR SEQ ID NO:25:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Ala Pro Gly Pro Ala Met Thr Arg Glu Gly
 1               5                  10
```

(2) INFORMATION FOR SEQ ID NO:26:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
Ala Pro Arg Pro Ala Asn Gln Arg Val Gly
 1               5                  10
```

(2) INFORMATION FOR SEQ ID NO:27:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
Ala Pro Val Gln Ala Leu Gln Gln Ala Gly
 1               5                  10
```

(2) INFORMATION FOR SEQ ID NO:28:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

```
Ala Pro Gly Gln Ala Leu Gln Arg Val Gly
1               5                   10
```

(2) INFORMATION FOR SEQ ID NO:29:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

```
Asp Asp Asp Asp Lys
1               5
```

(2) INFORMATION FOR SEQ ID NO:30:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
Asp Tyr Lys Asp Asp Asp Asp Lys
1               5
```

(2) INFORMATION FOR SEQ ID NO:31:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

```
Val Arg Pro Val Lys Ser Phe Arg
1               5
```

(2) INFORMATION FOR SEQ ID NO:32:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

```
Ser Leu Ser Ser Arg Gln Ser Pro
1               5
```

(2) INFORMATION FOR SEQ ID NO:33:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

Ser Pro Arg Pro Arg Ser Thr Pro
1               5

(2) INFORMATION FOR SEQ ID NO:34:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

Gln Arg Thr Lys Arg Lys His Asn
1               5

(2) INFORMATION FOR SEQ ID NO:35:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

Gly Pro Arg Leu Arg His Pro Arg
1               5

(2) INFORMATION FOR SEQ ID NO:36:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

Asn Leu Arg Lys Arg Lys Ile Lys
1               5

(2) INFORMATION FOR SEQ ID NO:37:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

Asn Ser Thr Val Arg Lys Arg Lys
1               5

(2) INFORMATION FOR SEQ ID NO:38:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

```
Pro Pro Pro Phe Arg Arg Ser Ser
1               5
```

(2) INFORMATION FOR SEQ ID NO:39:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

```
Pro Leu Ile Leu Arg Ser Arg Ala
1               5
```

(2) INFORMATION FOR SEQ ID NO:40:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

```
Lys Lys Ile Glu Arg Arg Asn Thr
1               5
```

(2) INFORMATION FOR SEQ ID NO:41:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

```
Gln Lys Arg Gly Arg Glu Pro Arg
1               5
```

(2) INFORMATION FOR SEQ ID NO:42:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

```
Glu Glu Lys Lys Lys His Lys Lys
1               5
```

(2) INFORMATION FOR SEQ ID NO:43:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

Arg Gln Asn Arg Arg Pro Ser Asn
1               5

(2) INFORMATION FOR SEQ ID NO:44:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

Val Arg Pro Ala Arg Ala Leu His
1               5

(2) INFORMATION FOR SEQ ID NO:45:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:45:

Leu Ile Ala Leu Arg Ser Thr Thr
1               5

(2) INFORMATION FOR SEQ ID NO:46:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

Pro Thr Pro Leu Lys His Pro Arg
1               5

(2) INFORMATION FOR SEQ ID NO:47:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:47:

Pro Tyr Pro Pro Lys Arg Thr Pro
1               5

(2) INFORMATION FOR SEQ ID NO:48:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:48:

```
Leu Ser Thr Ser Arg Ala Ser Ile
1               5
```

(2) INFORMATION FOR SEQ ID NO:49:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:49:

```
Thr Gly Val His Lys Pro Ser Thr
1               5
```

(2) INFORMATION FOR SEQ ID NO:50:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

```
Leu Cys Ala Lys Arg Leu Tyr Arg
1               5
```

(2) INFORMATION FOR SEQ ID NO:51:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:51:

```
Arg Lys Pro Thr Lys Lys Asn Ser
1               5
```

(2) INFORMATION FOR SEQ ID NO:52:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:52:

```
Glu Cys Arg Gln Arg His Thr Arg
1               5
```

(2) INFORMATION FOR SEQ ID NO:53:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:53:

```
Ser Leu Ala Leu Arg Val Trp Arg
1               5
```

(2) INFORMATION FOR SEQ ID NO:54:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:54:

```
Gly Pro Arg Leu Arg His Pro Arg
1               5
```

(2) INFORMATION FOR SEQ ID NO:55:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:55:

```
Phe Ile Ser Arg Arg Val Cys Arg
1               5
```

(2) INFORMATION FOR SEQ ID NO:56:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:56:

```
Pro Asp Asn Gln Arg Tyr Ile Thr
1               5
```

(2) INFORMATION FOR SEQ ID NO:57:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

```
Pro Leu Pro Cys Lys Leu Asp Ala
1               5
```

(2) INFORMATION FOR SEQ ID NO:58:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:58:

```
Ile Arg Phe Ala Arg Ser Gln Ala
  1               5
```

(2) INFORMATION FOR SEQ ID NO:59:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:59:

```
Pro Thr Pro Leu Lys His Pro Arg
  1               5
```

(2) INFORMATION FOR SEQ ID NO:60:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:60:

```
Pro Phe Thr His Lys Ser Leu Ser
  1               5
```

(2) INFORMATION FOR SEQ ID NO:61:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:61:

```
Ser Val Leu Pro Lys Leu Arg Ile
  1               5
```

(2) INFORMATION FOR SEQ ID NO:62:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:62:

```
Pro Lys Glu Thr Lys Gln Thr Asn
  1               5
```

(2) INFORMATION FOR SEQ ID NO:63:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:63:

-continued

```
Ser Leu Ser Ser Arg Gln Ser Pro
1               5
```

(2) INFORMATION FOR SEQ ID NO:64:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:64:

```
Thr Pro Leu Leu Lys Ser Trp Leu
1               5
```

(2) INFORMATION FOR SEQ ID NO:65:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:65:

```
Arg Asn Arg Gln Lys Thr Asn Asn
1               5
```

MAST CELL PROTEASE PEPTIDE INHIBITORS

RELATED APPLICATIONS

This application claims priority under 35 USC § 119(e) from U.S. Provisional Patent Application Serial No. 60/037,090, filed on Feb. 5, 1997, entitled MAST CELL PROTEASE PEPTIDE INHIBITORS. The contents of the provisional application are hereby expressly incorporated by reference.

GOVERNMENT SUPPORT

This work was funded in part by grant numbers AI-23483, and HL-36110 from the National Institutes of Health. Accordingly, the United States Government may have certain rights to this invention.

FIELD OF THE INVENTION

This invention relates to compositions containing a mast cell protease inhibitor and methods for use thereof in the prevention and treatment of inflammatory disorders mediated by mast cell tryptases. Methods utilizing the compositions for identifying additional inhibitors of the mast cell protease also are provided.

BACKGROUND OF THE INVENTION

Mast cells play central roles in varied inflammatory reactions due to their ability to release a diverse array of biologically active factors. During the last decade, the primary focus has been on the role of mast cell-derived histamine, leukotrienes, prostaglandins, cytokines, and chemokines in inflammation. Little attention has been paid to the role of tryptases even though these serine proteases are major constituents of the secretory granules of human, mouse, rat, gerbil, and dog mast cells. Accordingly, the mechanisms by which mast cell tryptases mediate inflammation have not been identified.

All mast cell proteases are targeted to the secretory granule as inactive zymogens but they are rapidly activated at this site. Thus, they are stored in the granule in their mature, enzymatically active forms. Tryptases, the major secretory granule proteases of human mast cells, are glycosylated, heparin-associated tetramers of heterogenous, catalytically active subunits. These enzymes are stored in an enzymatically inactive state in the mast cell's secretory granules and are released from the cell following activation through the high affinity IgE receptor. Tryptases have been implicated in a variety of biological processes including tissue inflammation.

Various attempts have been made to identify inhibitors of tryptase for treating inflammatory disorders. For example, small aromatic molecules have been proposed as tryptase inhibitors for preventing and treating inflammatory diseases associated with the respiratory tract, such as asthma and allergic rhinitis. (See, e.g., U.S. Pat. No. 5,525,623, issued to Spear et al., "Compositions and Methods for the Treatment of Immunomediated Inflammatory Disorders"; and International Application Nos. PCT/US95/11814, WO96/09297, and PCT/US94/02706, WO94/20527, Applicant: Arris Pharmaceutical Corporation.) Unfortunately, such molecules nonspecifically inhibit a variety of serine proteases (including pancreatic trypsin) that are present in vivo and, accordingly, the therapeutic value of such molecules for treating conditions mediated by mast cell tryptase remains questionable.

In view of the demonstrated involvement of mast cells in the initiation of inflammation, a need still exists to understand the mechanisms by which mast cells control such inflammation and to develop new and useful agents that inhibit or prevent inflammation in the first instance. Preferably, such agents would selectively inhibit specific components produced by the mast cell that are responsible for the inflammation, thereby requiring administration of relatively low doses of the agent and minimizing the likelihood of side reactions that may be associated with the administration of a high dosage of the agent.

SUMMARY OF THE INVENTION

The present invention overcomes the problems of the prior art by providing a preferred peptide substrate (protease inhibitor) and its derivatives which can be used to selectively inhibit aL mast cell tryptase that induces neutrophilia when administered to mice. The invention involves in one respect the discovery of a peptide sequence (SEQ. ID NO. 1) that is a substrate for a complex containing mouse mast cell protease 6 ("mMCP-6") and heparin glycosaminoglycan. This peptide sequence can be used to selectively inhibit this and related mast cell tryptase complexes in vitro and in vivo. Although not intending to be bound to a particular mechanism of action, it is believed that the human tryptases α, I, β/II, and III (GenBank Accession Nos. are shown in the sequence listing ) and rat tryptase (GenBank Accession No. U67909, J. Exp. Med. 1997; 185:13–29) are the homologs of mMCP-6 and that one or more of these human tryptases play a key role in the pathogenesis of mast cell-mediated inflammatory disorders including the emigration of neutrophils.

In view of the foregoing, the protease inhibitors of the invention are useful for treating a variety of inflammatory disorders including asthma, allergic rhinitis, urticaria and antioedema, eczematous dermatitis (atopic dermatitis), and anaphylaxis, as well as hyperproliferative skin disease, peptic ulcers, inflammatory bowel disorder, inflammatory skin conditions, and the like. The protease inhibitors of the invention also are useful in screening assays for identifying additional inhibitors that selectively inhibit tryptase-6 cleavage of a peptide having SEQ. ID NO.1.

It remains to be determined exactly how many tryptases exist in humans. Four human tryptase cDNAs (designated tryptase α, I, β/II, and III) were isolated by two groups of investigators using two different cDNA libraries (Miller et al., J. Clin. Invest. 1989; 84:1188–1195; Miller et al., J. Clin. Invest. 1990; 86:64–870; Vanderslice et al., Proc. Natl. Acad. Sci. USA 1990; 87:3811–3815). Since the isolated human cDNAs encode enzymes that are >90% identical in their overall amino acid sequences, since humans are not inbred, and since the genes and the region of the chromosome where the tryptase genes reside have not yet been sequenced, the actual number of human mast cell tryptase genes is still unknown. There may be one gene in the human possessing multiple alleles or there may be four or more tryptase genes, some of which are nearly identical. Nevertheless, most investigators believe that human tryptase α and β are derived from distinct genes.

In terms of their overall amino acid sequences, mature mMCP-7 and mMCP-6 are 71% identical. Mature mMCP-7 exhibits homologies with human tryptases α, I, β/II, and III of 74%, 76%, 76% and 78%, respectively, whereas mature mMCP-6 exhibits homologies of 73%, 78%, 78% and 78%, respectively. Thus, it is difficult to conclude from their overall amino acid sequences which tryptase is the human homolog of mMCP-6. However, a comparison of the pro-peptides of mMCP-6 (see below) with those of human tryptases α, I, β/II, and III indicate that human tryptase a probably is not the human homolog of mMCP-6. Comparative analysis of the seven loops that Dr. Šali predicts form the substrate binding pocket of each tryptase also indicates that human tryptase a probably is not the human homolog of mMCP-6. However, at present it is not possible to definitively conclude whether the pocket of mMCP-6 is more similar to that in tryptase I, β/II, or III.

peptide having SEQ. ID NO. 1 by a mast cell protease is provided. Preferably, the mast cell tryptase-6 is mMCP-6 or human tryptase that is complexed with a mast cell specific glycosaminoglycan (e.g., heparin or ChS-E glycosaminoglycan). In a particularly preferred embodiment, the mast cell tryptase-6 inhibitor is a peptide having the amino acid sequence: Arg-Asn-Arg-Gln-Lys-Thr (SEQ. ID NO.1). The invention also includes functionally equivalent peptides of SEQ. ID NO. 1, namely, (1) fragments (2) chemically modified forms of the peptide, and (3)

Comparison of the Pro-peptides of Mouse and Human Mast Cell Tryptases

| Tryptase | Propeptide (and residue number) -10                         -3    -1   +1 | | | | |
|---|---|---|---|---|---|
| mMCP-7 | Ala-Pro-Gly-Pro-Ala-Met-Thr-Arg-Glu-Gly | --- | Mature enzyme | (SEQ ID NO. 25) |
| mMCP-6 | Ala-Pro-Arg-Pro-Ala-Asn-Gln-Arg-Val-Gly | --- | Mature enzyme | (SEQ ID NO. 26) |
| h tryptase α | Ala-Pro-Val-Gln-Ala-Leu-Gln-Gln-Ala-Gly | --- | Mature enzyme | (SEQ ID NO. 27) |
| h tryptase I | Ala-Pro-Gly-Gln-Ala-Leu-Gln-Arg-Val-Gly | --- | Mature enzyme | (SEQ ID NO. 28) |
| h tryptase II/β | Ala-Pro-Gly-Gln-Ala-Leu-Gln-Arg-Val-Gly | --- | Mature enzyme | (SEQ ID NO. 28) |
| h tryptase III | Ala-Pro-Gly-Gln-Ala-Leu-Gln-Arg-Val-Gly | --- | Mature enzyme | (SEQ ID NO. 28) |

As used herein, "tryptase-6", and "mast cell tryptase" are used interchangeably to refer to an enzymatically active serine protease that selectively cleaves a peptide sequence having SEQ. ID NO.1. The preferred tryptase-6 for use in the screening assays of the invention is the mature mMCP-6 tryptase or the corresponding mature human tryptase. The nucleic acid and encoded protein sequence of the mMCP-6 zymogen from BALB/c mice are provided as SEQ. ID NOS.13, 14 and 15, and have been accorded GenBank Accession Nos. M57625 and M57626 (see also Reynolds, et al., J. Biol. Chem. 1991, 266:3847–3853). The GenBank accession numbers and reference citations for these and related mast cell protease nucleic acids and/or proteins are provided in the Sequence Listing. In particular, the Sequence Listing identifies the nucleic acid and encoded protein sequence of the potential human homolog(s) of the mMCP-6 zymogen (SEQ. ID NOS. 16–23). These protein sequences include the sequence of the "mature" tryptase-6 proteins. By "mature", it is meant that the sequence represents the serine protease which is the enzymatically active form of the protein (i.e., the form that associates with heparin glycosaminoglycan to form the tryptase-6 complex that selectively cleaves SEQ. ID NO. 1).

In general, the enzymatically active serine proteases of the invention are associated with a mast cell specific glycosaminoglycan such as heparin in a complex that can be formed in vitro and is also known to exist in vivo. Surprisingly, association of a glycosaminoglycan, such as heparin glycosaminoglycan, with the tryptase-6 appears to be essential for the peptide substrate specificity of the cleavage reaction. The Examples demonstrate the extraordinary specificity of an mMCP-6 tryptase/heparin glycosaminoglycan complex for cleaving SEQ. ID NO. 1 and the lack of specificity for mMCP-6 in the absence of this glycosaminoglycan. Prior to this discovery, the dependence of mMCP-6 cleavage specificity on an association with heparin glycosaminoglycan was unknown and could not have been predicted in view of the reported nonspecific cleavage properties of this tryptase or its homologs in other species.

According to one aspect of the invention, a mast cell tryptase-6 inhibitor that competitively inhibits cleavage of a homologs of SEQ I.D. No. 1 that can be used in accordance with the methods of the invention to selectively inhibit a mast cell tryptase-6 complex in vitro or in vivo. Functionally equivalent peptides contain from three to twelve amino acids and are capable of inhibiting the specific cleavage of SEQ. ID NO. 1 by a mast cell tryptase-6 complex, i.e., tryptase-6 associated with a serglycin proteoglycan.

According to one aspect of the invention, a method for inhibiting a mast cell tryptase-6 complex that selectively cleaves SEQ. ID NO. 1 is provided. The method involves contacting the mast cell tryptase-6 complex with one or more protease inhibitors of the invention for a time sufficient to permit the protease inhibitor to enter the substrate binding site of the enzyme.

According to still another aspect of the invention, a method for selecting a mast cell tryptase-6 complex inhibitor is provided. The method involves determining whether a mast cell tryptase-6 complex cleaves a peptide having SEQ. ID NO. 1 in the presence of a putative protease inhibitor. In a particularly preferred embodiment, the putative protease inhibitor is contained in a phage display library. These methods (also referred to herein as "screening assays") are useful for identifying the above-mentioned functionally equivalent peptides of SEQ. ID NO. 1. Such screening assays rely upon biochemical measurements, physical measurements or functional activity tests to determine whether cleavage of SEQ. ID NO. 1 has occurred.

Exemplary functionally equivalent peptide fragments of SEQ. ID NO. 1 are provided in SEQ. ID NOS. 2–11. Exemplary functionally equivalent homologs of SEQ. ID NO. 1 are derived from the naturally-occurring proteins that contain SEQ. ID NO. 1 or a sequence that is substantially identical to SEQ. ID NO. 1. Functionally equivalent peptides of SEQ. ID NO. 1 optionally contain from one to six conservative amino acid substitutions.

The protease inhibitors of the invention competitively inhibit cleavage by a mast cell tryptase-6 of SEQ. ID NO. 1. The preferred protease inhibitors of the invention are irreversible competitive inhibitors. Such irreversible protease inhibitors include, for example, a derivatizing, agent that reacts with an amino acid in the substrate binding site of the mast cell protease to form a covalent bond. Preferably, such derivatizing agents can reside anywhere in the protease inhibitor. In general, such irreversible protease inhibitors have a structure that mimics the transition state of the enzyme-substrate complex formed during reaction of the mast cell protease with SEQ. ID NO. 1. According to yet other aspects of the invention, pharmaceutical compositions containing the above-described protease inhibitors and methods for making the pharmaceutical compositions are provided. The methods involve placing the protease inhibitors of the invention in a pharmaceutically acceptable carrier.

According to a related aspect of the invention, a method for treating a mast cell-mediated inflammatory disorder is provided. Exemplary mast cell-mediated inflammatory disorders include asthma, allergic rhinitis, urticaria and antioedema, and eczematous dermatitis (atopic dermatitis), and anaphylaxis, as well as hyperproliferative skin disease, peptic ulcers, inflammatory bowel disorder, inflammatory skin conditions, and the like. Such mast cell-mediated inflammatory disorders are believed by the Applicants to be mediated by a tryptase-6. Accordingly, the method of the invention involves administering to a subject in need of such treatment one or more protease inhibitors of the invention in a pharmaceutically acceptable carrier. The protease inhibitor is administered to the subject in an amount effective to inhibit activity of a mast cell tryptase-6 complex in said subject.

These and other aspects of the invention as well as various advantages and utilities will be more apparent with reference to the detailed description of the preferred embodiments and in the accompanying drawings. All patents, patent publications and references identified in this document are incorporated in their entirety herein by reference.

DETAILED DESCRIPTION OF THE INVENTION

The present invention in one aspect involves the discovery that a macromolecular complex containing mouse mast cell tryptase-6 ("mMCP-6") associated with heparin glycosaminoglycan selectively cleaves a peptide having the sequence of SEQ. ID NO. 1 and that this and other structurally-related peptides can be used to selectively inhibit the enzymatic activity of mMCP-6 and its homologs (e.g., human tryptase) in vitro and in vivo. Although not intending to be bound to any particular mechanism or theory, it is believed that the naturally-occurring ("physiological") substrate(s) of tryptase in vivo contains a peptide sequence that is substantially identical to SEQ. ID NO. 1 and that cleavage by a tryptase-6 in vivo of its physiological substrate represents a fundamental step in the pathogenesis of mast cell mediated-inflammatory disorders. By "substantially identical" it is meant that the peptide cleavage site sequence of the physiological substrate of tryptase-6 differs from SEQ. ID NO. 1 by, at most, one amino acid.

As used herein, a "tryptase-6" protein refers to the enzymatically active "mature" mMCP-6 protein, its naturally occurring alleles, and homologs of the foregoing proteins in other species. The tryptase-6 proteins, like other serine proteases, are synthesized in cells as zymogens (i.e., in an enzymatically inactive precursor form) which include a hydrophobic "pre" peptide sequence (also referred to as a "signal sequence" or "signal peptide") and a "pro" sequence (also referred to as a "pro-peptide sequence") attached to the N-terminal portion of the mature protein. The nucleic acid and encoded protein sequence of the mMCP-6 zymogen from BALB/c mice are provided as SEQ ID NOS. 13, 14 and 15, and have been accorded GenBank Accession Nos. M57625 and M57626, (see also Reynolds, et al., J. Biol. Chem. 1991, 266:3847–3853). The GenBank accession numbers and reference citations for these and other mast cell protease nucleic acids and/or proteins are provided in the Sequence Listing. In particular, the Sequence Listing identifies the nucleic acid and encoded protein sequence of the potential human homologs of the mMCP-6 zymogen (SEQ ID NOS. 16–23), including the protein sequences for the "mature" tryptase-6 proteins for these proteins. By "mature", it is meant that the sequence represents the serine protease which is the enzymatically active form of the protein.

The tryptase-6 proteins that are inhibited by the protease inhibitors of the invention are members of the serine protease superfamily. In particular, the tryptase-6 proteins are members of the trypsin-like serine protease family of proteins that are the major constituents of the secretory granules of mouse, rat, gerbil, dog, and human mast cells. Lung, heart, and skin mast cells in the BALB/c mouse express at least two tryptases [designated mouse mast cell protease 6 ("mMCP-6") and 7 ("mMCP-7")] which are 71% identical in terms of their overall amino acid sequences. This tryptase family of mast cell proteases has been implicated in the pathobiology of FcεRI-elicited responses in airways. Linkage analysis has implicated the region of chromosome 17 where the mMCP-6 and mMCP-7 genes reside as one of the candidate loci for the inheritance of intrinsic airway hyper responsiveness. A physiological substrate for the mMCP-7 protein recently has been identified as fibrinogen (see, U.S. Ser. No. 60/032,354 filed Dec. 4, 1996, now U.S. Ser. No.08/978,404 filed Nov. 25, 1997 by R. Stevens). To date, the inability to definitively identify the physiological substrate for mMCP-6 has prevented the development of therapeutic agents that mediate conditions attributable to an under- or over-abundance of the mMCP-6 protein or its physiological substrate. Accordingly, the identification of the specific cleavage sequence disclosed herein for the mMCP-6 protein permits the development of therapeutic agents for treating conditions that are mediated by this tryptase.

The mMCP-6 protein is stored in acidic granules of the cell as a complex containing the mature, enzymatically active form of the enzyme ionically bound to the glycosaminoglycan side chains of serglycin proteoglycans (Ghildyal, et al., J. Exp. Med. 1996; 184:1061–1073, whose content is incorporated herein by reference in its entirety). As used herein, a "tryptase-6 complex" refers to a mature mMCP-6 tryptase (its alleles, homologs) in association with a serglycin proteoglycan (containing heparin or another mast cell-specific chondroitin). Although mMCP-6 and mMCP-7 are negatively charged at neutral pH and are associated with serglycin proteoglycans at neutral pH, the two tryptases differ in their ability to dissociate from the proteoglycans following their exocytosis from the mast cell. As a result, these proteases exhibit different substrate specificities and are metabolized quite differently in mice undergoing passive systemic anaphylaxis.

Modeling and site-directed mutagenesis analysis of recombinant pro-mMCP-7 (i.e., the expressed protein with its normal "pro-peptide" sequence) suggest that this mature tryptase readily dissociates from serglycin proteoglycans when the protease/proteoglycan macromolecular complex is exocytosed into a pH 7.0 environment because the glycosaminoglycan-binding domain on the surface of mMCP-7 consists primarily of a cluster of His residues. In contrast, the mMCP-6 protein does not readily dissociate from serglycin proteoglycans because its glycosaminoglycan-binding domain consists primarily of a cluster of strongly basic Lys or Arg residues, as found in all mast cell chymases. Although not intending to be limited to a particular mechanism of action, the prolonged retention of exocytosed mMCP-6 complex in the extracellular matrix around activated tissue mast cells is believed by us to be associated with a local activity for this tryptase, whereas the rapid dissipation of mMCP-7 from tissues and its poor ability to be inactivated by circulating protease inhibitors suggests that this distinct, but homologous, tryptase cleaves proteins at more distal sites.

More than 25 genes have been cloned that encode the peptide cores of different proteoglycans. mMCP-6 is preferentially bound to the glycosaminoglycan (GAG) side chains of the serglycin family of proteoglycans. Those mast cells that express mMCP-6 generally have serglycin proteoglycans that have covalently bound heparin chains but sometimes these proteoglycans have highly charged chondroitin sulfate (ChS) chains (e.g., ChS-diB and ChS-E) Human lung mast cells also can express serglycin proteoglycans that can have either heparin or ChS-E chains (Stevens et al., Proc. Natl. Acad. Sci. USA 1988; 85:2284–2287). Although small amounts of serglycin proteoglycan containing ChS-E chains have been identified in cultured human eosinophils (Rothenberg et al., J. Biol. Chem. 1988; 263:13901–13908), mast cells are the only mammalian cell type which can produce relatively large amounts of ChS-E.

It is not known why mast cells synthesize very different types of GAG onto a serglycin peptide core. Since more than 30 enzymes are involved in the differential biosynthesis of heparin and ChS-E, the switch in GAG expression in the mast cell probably is biologically relevant. It is possible that ChS-E influences the substrate specificity of mMCP-6 differently than heparin. Accordingly, other highly charged GAG, such as ChS-E, also may regulate the substrate specificity of mMCP-6.

The specificity of the mMCP-6 complex for cleaving SEQ. ID NO. 1 was discovered during experiments designed to elucidate the preferred amino acid sequences that are cleaved by this mast cell protease. Surprisingly, heparin glycosaminoglycan was found to alter the substrate specificity of mMCP-6 for cleaving peptides in a tryptase-specific bacteriophage display library. We believe that heparin glycosaminoglycan may sterically restrict the substrate-binding cleft of mMCP-6 by directly influencing one of the seven loops that form this pocket. The present invention is based upon the discovery that the mMCP-6 complex selectively cleaves a peptide containing SEQ. ID NO. 1 but that this enzymatic activity is not shared with mMCP-6 (in the absence of a serglycin proteoglycan) or with mMCP-7.

A "mast cell protease inhibitor" or a "protease inhibitor", as used herein, refers to a peptide which competitively inhibits cleavage by a tryptase-6 complex of SEQ. ID NO. 1. The protease inhibitors of the invention are peptides that are or contain SEQ. ID NO. 1 or its functionally equivalent peptides. Protease inhibitors which are functionally equivalent peptides of SEQ. ID NO. 1 are identified in screening assays which measure the ability of a putative protease inhibitor to prevent cleavage by a tryptase-6 complex (e.g., a mMCP-6 or human tryptase-6 complex) of SEQ. ID NO. 1 or its functional equivalents.

As used herein, "functionally equivalent peptides" of SEQ. ID NO.1 refer to (1) fragments, (2) chemicallly modified derivatives, and (3) homologs of SEQ. ID NO. 1, that can be used in accordance with the methods of the invention to inhibit cleavage by a tryptase-6 complex of SEQ. ID NO. 1. Functionally equivalent peptides contain from three to twelve amino acids and competitively inhibit cleavage by a tryptase-6 complex of a peptide that is or that includes SEQ. ID NO.1.

Functionally equivalent peptides of SEQ. ID NO. 1 are identified in one or more "screening assays". In general, such screening assays are of two types: (1) binding assays which detect a complex containing the putative protease inhibitors associated with a tryptase-6 complex (e.g., mMCP-6/heparin glycosaminoglycan) and (2) enzymatic activity assays which measure the ability of a putative protease inhibitor to inhibit cleavage by a tryptase-6 complex of SEQ. ID NO. 1 or a functionally equivalent peptide of SEQ. ID NO. 1. In general, the binding assays (preferably, irreversible binding) involve the detection of a labeled inhibitor (e.g., a fluorescent or radioactive tag) associated with the tryptase-6 complex; enzymatic assays measure the ability of the putative protease inhibitor to competitively inhibit cleavage by the tryptase-6 complex of SEQ. ID NO. 1.

In a particularly preferred embodiment, the protease inhibitor of the invention has SEQ. ID NO. 1. This amino acid sequence was identified in a tryptase-specific bacteriophage peptide display library that was screened with mMCP-6 to determine its preferred substrate peptide sequence (see Example). No particular peptide sequence was favored when the library was screened with mMCP-6 alone; however, a phage clone was preferentially obtained when the library was screened with an mMCP-6/heparin complex. Analysis of this clone revealed a sequence (SEQ. ID NO. 1) that was susceptible to cleavage by the mMCP-6/heparin complex. A search of GenBank indicated that a sequence that is substantially identical to SEQ. ID No. 1 is present in human fibronectin (SEQ. ID NO. 12, amino acid nos. 1351–1356). Although not intending to be bound to any particular theory or mechanism, it is believed that this protein represents a physiological substrate of human tryptase-6 and that tryptase-6 mediates the pathogenesis of inflammatory disorders by selectively cleaving fibronectin at an amino acid sequence that is substantially identical to SEQ. ID NO. 1. (See Example for a more detailed discussion of the role played by fibronectin in integrin-binding and the implications of this discovery with respect to the role played by tryptase in mast-cell mediated inflammation by controlling integrin-dependent signaling pathways.)

The amino acid sequence of SEQ. ID NO. 1 is:

Arg-Asn-Arg-Gln-Lys-Thr (SEQ.ID NO. 1).

A generic formula that embraces SEQ. ID NO. 1 is:

R/K-X-R/K-X-R/K-X, where R/K represents an Arg or Lys (basic amino acids)and X represents a neutral amino acid. It is believed that the highly charged basic character of SEQ. ID NO. 1 plays an important role in the localization of the peptide to substrate binding site of the mast cell tryptase-6.

As used herein, functionally equivalent "peptide fragments" of SEQ. ID NO. 1 refer to fragments of SEQ. ID NO. 1 that contain from three to five amino acids (SEQ. ID NOS. 2 through 10). Peptide fragments can be synthesized without undue experimentation using standard procedures known to those of ordinary skill in the art. Each of SEQ. ID NOS. 2–10 contains at least one basic amino acid that can serve as a P1 amino acid for cleavage by the mast cell serine protease.

In general, the term "homolog" refers to a molecule that shares a common structural feature with the molecule to which it is deemed to be an homolog. As used herein in reference to the protease inhibitors of the invention, a "functionally equivalent peptide" that is a "homolog" of SEQ. ID NO.1 is a peptide which shares a common structural feature (amino acid sequence homology) and a common functional activity (inhibiting tryptase-6 complex cleavage of SEQ. ID NO.1) with SEQ. ID NO.1. Functionally equivalent peptide homologs of SEQ. ID NO.1 are derived from naturally-occurring proteins that contain an amino acid sequence having sequence homology to SEQ. ID NO.1. Preferably, such homologs contain at least four and, preferably, five of the amino acid residues in the same order as SEQ. ID NO.1 and, optionally, contain from zero to five amino acids that are derived from the naturally-occurring amino acid sequence. Exemplary functionally equivalent peptide homologs of SEQ. ID NO. 1 include amino acids 1351–1356, 1350–1356, 1349–1356, 1348–1356, 1347–1356, 1346–1356, 1351–1357, 1351–1358, 1351–1359, 1351–1360, 1351–1361- and 1346–1361 of fibronectin (SEQ. ID No. 12).

A computer search of a protein database with SEQ. ID NO.1 revealed a substantially identical sequence in fibronectin. Athough not intending to be bound to any particular theory, it is believed that the physiological substrate for mMCP-6 complex is fibronectin and that tryptase-6 complex is capable of selectively cleaving this protein in vitro or in vivo. Thus, fibronectin represents a "protein homolog" of SEQ. ID NO.1 from which functionally equivalent peptide homologs of SEQ. ID NO. 1 can be derived.

Fibronectin contains the sequence, Arg-Gly-Arg-Gln-Lys-Thr (SEQ. ID NO.11), which differs from SEQ. ID NO.1 in a single amino acid. This sequence is found in fibronectin at amino acids 1351–1356 and is believed to be a cleavage site for the mast cell serine protease in vivo. Functionally equivalent peptide homologs of SEQ. ID NO.1 that are derived from fibronectin include from zero to five amino acids that are N-terminal and/or C-terminal to SEQ. ID NO.11 in the this protein homolog. Additional SEQ. ID NO.1 protein homologs having sequence homology with SEQ. ID NO.1 can be identified using art-recognized methods, e.g., searching data bases such as GENBANK for homologous peptides and/or proteins, as new sequences are added to these databases.

Functionally equivalent peptides of SEQ. ID NO.1 optionally contain conservative amino acid substitutions, provided that the peptides which contain the conservative substitutions competitively inhibit SEQ. ID NO.1 binding to, or cleavage by, a mast cell tryptase-6 complex in the above-mentioned screening assays. As used herein, "conservative amino acid substitution" refers to an amino acid substitution which does not alter the relative charge or size characteristics of the peptide in which the amino acid substitution is made. Conservative substitutions of amino acids include substitutions made amongst amino acids within the following groups: (a) M,I,L,V; (b) F,Y,W; (c) K,R,H; (d) A,G; (e) S,T; (f) Q,N; and (g) E,D. In the particularly preferred embodiments, the functionally equivalent peptides of SEQ. ID NO. 1 include one or more conservative amino acid substitution in which arginine and lysine are substituted for one another. It is believed that one, two, or three conservative amino acid substitutions can be made in SEQ. ID NO. 1 without adversely affecting the ability of the peptide to competitively bind to/inhibit a tryptase-6 complex.

Preferably, the protease inhibitors of the invention are peptides that include one or more inter-amino acid bonds that are non-hydrolyzable in vivo. For example, the peptide may contain one or more D-amino acids, thereby rendering the peptide less susceptible to non-specific proteolytic cleavage in vivo. Alternatively, or additionally, the peptide may contain a non-hydrolyzable peptide bond. Such non-hydrolyzable peptide bonds and methods for preparing peptides containing same are known in the art. Exemplary non-hydrolyzable bonds include -psi[$CH_2NH$]-reduced amide peptide bonds, -psi[$COCH_2$]- ketomethylene peptide bonds, -psi[$CH(CN)NH$]-(cyanomethylene)amino peptide bonds, -psi[$CH_2CH(OH)$]- hydroxyethylene peptide bonds, -psi[$CH_2O$]- peptide bonds, and -psi[$CH_2S$]- thiomethylene peptide bonds. Additional non-hydrolyzable peptide bonds can be identified using no more than routine experimentation.

In the preferred embodiments, a derivatizing agent (X) is covalently coupled to the peptide substrate (protease inhibitor) to form an irreversible protease inhibitor (X-P P). Preferably, the derivatizing agent is covalently attached to the N-terminal or the C-terminal amino acid of the protease inhibitor in accordance with standard procedures for derivatizing an amino acid. In general, the derivatizing agent is a reactive group that reacts with an amino acid in the substrate binding site of the mast cell tryptase-6 complex. Preferably, the chemically modified derivative of the peptide substrate (protease inhibitor) possesses a reactive group that functions as an irreversible inhibitor of a tryptase-6 (e.g., mMCP-6). For example, numerous low molecular weight inhibitors of serine proteases have been synthesized that contain a α-fluorinated ketone or α-keto ester derivative of a critical amino acid in the preferred peptide substrate (Angelastro et al., J. Med. Chem. 1990; 33:13–16). Additional exemplary derivatizing agents for conferring upon a peptide substrate the ability to irreversibly bind to the substrate binding site are described in U.S. Pat. No. 5,543,396, issued to Powers, et al., "Proline Phosphonate Derivative"; and U.S. Pat. No. 5,187,157 and U.S. Pat. No. 5,242,904, issued to Kettner, et al., "Peptide Boronic Acid Inhibitors of Trypsin-Like Proteases".

As discussed above, a computer search of a protein database with SEQ. ID NO.1 revealed that a substantially identical sequence (SEQ. ID NO. 11, fibronectin amino acids 1351–1356) resides in the middle of each subunit of fibronectin. This sequence is conserved from rats to humans. As discussed in detail in the Example, fibronectin possesses numerous conserved domains that enable fibronectin to interact simultaneously with different proteins on the cell's surface and in the extracellular matrix. The mMCP-6 susceptible sequence in fibronectin is located between the collagen and integrin binding domains. Based upon this observation and the results disclosed herein, we believe that specific cleavage at this site has a dramatic effect on fibronectin-mediated adhesion of fibroblasts and inflammation that is mediated by integrin signal transduction.

Described in the Example is an experiment in which mMCP-6 was injected into the peritoneal cavity of a mouse animal model. Surprisingly, the injection of mMCP-6 into the peritoneal cavity of the animal model specifically recruited neutrophils to this site; however, injection of homologous mMCP-7 into the cavity did not have this effect. As discussed in more detail in the Example, we believe that neutrophil emigration in this in vivo assay is mediated, in part, by a generated large-sized fragment of fibronectin that lacks its collagen binding domain. Accordingly, the discovery described herein that mMCP-6 (but not mMCP-7) specifically cuts fibronectin between its collagen- and integrin-binding domains has important implications for mast cell-mediated control of fibrosis and inflammation. More specifically, the animal model results presented herein provide evidence that the protease inhibitors disclosed herein are useful for modulating tryptase-6-mediated inflammation by inhibiting specific cleavage by tryptase of its physiological substrate in vivo. Although mMCP-6 and mMCP-7 (described in U.S. Ser. No. 60/032, 354) have different substrate specificities, we believe that both tryptases alter integrin-mediated signaling pathways: mMCP-7 by cleaving fibrinogen and mMCP-6 by cleaving fibronectin. Thus, the results presented herein further suggest that mast cell tryptases play a central role in mast cell-mediated inflammation by controlling different integrin-dependent signaling pathways.

In view of the foregoing, a method for treating a mast cell-mediated inflammatory disorder is provided. The method involves administering to a subject in need of such treatment the tryptase-6 complex inhibitors of the invention in a pharmaceutically acceptable carrier and in an amount effective to inhibit activity of a tryptase-6 complex in said subject.

As used herein, a "mast cell-mediated inflammatory disorder" refers to those diseases associated with mast cell tryptase-6 release and susceptible to treatment with a tryptase-6 inhibitor such as disclosed herein. Examples of such disorders include diseases of immediate type hypersensitivity such as asthma, allergic rhinitis, urticaria and antioedema, and eczematous dermatitis (atopic dermatitis), and anaphylaxis, as well as hyperproliferative skin disease, peptic ulcers, inflammatory bowel disorder, inflammatory skin condiitons, and the like. "Hyperresponsiveness" refers to late phase bronchoconstriction and airway hyperreactivity associated with chronic asthma. Hyperresponsiveness of asthmatic bronchiolar tissue is believed to result from chronic inflammation reactions, which irritate and damage the epithelium lining the airway wall and promote pathological thickening of the underlying tissue. Thus, the protease inhibitors of the invention are useful for the treatment (prevent, delay the onset of, or ameliorate the symptoms) of immunomediated inflammatory disorders, and particularly with those associated with the respiratory tract, e.g., asthma, and hyperresponsiveness.

The protease inhibitors described above are administered in effective amounts. An effective amount is a dosage of the protease inhibitor sufficient to provide a medically desirable result. The effective amount will vary with the particular condition being treated, the age and physical condition of the subject being treated, the severity of the condition, the duration of the treatment, the nature of the concurrent therapy (if any), the specific route of administration and like factors within the knowledge and expertise of the health practioner. For example, an effective amount for treating asthma would be an amount sufficient to lessen or inhibit one or more clinically recognized symptoms of asthma. Thus, it will be understood that the protease inhibitors of the invention can be used to treat mast-cell mediated inflammatory disorders prophylactically in subjects at risk of developing such inflammatory disorders. As used in the claims, "inhibit" embraces all of the foregoing. Likewise, an effective amount for treating any of the above-noted inflammatory disorders is that amount which can slow or halt altogether the particular symptoms of such disorders. It is preferred generally that a maximum dose be used, that is, the highest safe dose according to sound medical judgment.

Generally, doses of active compounds will be from about 0.01 mg/kg per day to 1000 mg/kg per day. It is expected that doses in the range of 50–500 mg/kg will be suitable, preferably orally and in one or several administrations per day. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. As used herein, tryptase-6 inhibitor or protease inhibitor means the compounds described above as well as salts thereof.

The tryptase-6 inhibitors may be combined, optionally, with a pharmaceutically-acceptable carrier. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being comingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

Compositions suitable for parenteral administration conveniently comprise a sterile aqueous preparation of the protease inhibitor, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule.

The pharmaceutical compositions may conveniently be presented in unit dosage form and may be prepared by any of the methods well-known in the art of pharmacy. All methods include the step of bringing the protease inhibitors into association with a carrier which constitutes one or more accessory ingredients. In general, the compositions are prepared by uniformly and intimately bringing the protease inhibitors into association with a liquid carrier, a finely divided solid carrier, or both, and then, if necessary, shaping the product.

For topical applications, the protease inhibitors can be formulated as ointments or creams. Exemplary pharmaceutically acceptable carriers for peptide drugs, described in U.S. Pat. No. 5,211,657, are useful for containing the protease inhibitors of the invention. Exemplary pharmaceutically acceptable carriers for protease inhibitors that are small molecules and, in particular, for aerosol administration, are described in U.S. Pat. No. 5,525,623. Such preparations also are useful for containing the protease inhibitors of the invention. As used herein, the term "aerosol" refers to a gas-borne suspended phase of the protease inhibitors that is capable of being inhaled into the bronchioles or nasal passages. Such formulations are particularly useful for treating asthma and hyperresponsiveness.

According to another aspect of the invention, the protease inhibitors of the invention are useful as agents for modulating integrin-mediated signal transduction. Thus, the invention advantageously provides mast cell protease inhibitors in a form that can be administered in accordance with art-recognized methods for drug delivery in vivo. For example, the protease inhibitors can be formulated into an aerosol or topical pharmaceutic preparation to deliver to local cells an amount of protease inhibitor sufficient to inhibit mast cell-mediated fibrosis, inflammation, and integrin-related signal transduction pathways such as those involved in cell trafficking and proliferation. Topical application to the skin of a protease inhibitor of the invention is useful for inhibiting cell proliferation associated with conditions such as psoriasis. Aerosol application of a protease inhibitor is useful for inhibiting inflammation associated with asthma and other disorders associated with intrinsic airway hyperresponsiveness.

Compositions suitable for oral administration may be presented as discrete units, such as capsules, tablets, lozenges, each containing a predetermined amount of the protease inhibitors. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the protease inhibitors described above, increasing convenience to the subject and the physician. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the protease inhibitor is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

According to yet another aspect of the invention, a method for manufacturing a pharmaceutical composition containing the protease inhibitors of the invention is provided. The method involves placing the above-described protease inhibitor in a pharmaceutically acceptable carrier to form a pharmaceutical composition and administering the pharmaceutical composition containing a therapeutically effective amount of the protease inhibitor to the recipient.

It should be understood that the preceding is merely a detailed description of preferred embodiments. It therefore should be apparent to those of ordinary skill in the art that various modifications and equivalents can be made without departing from the spirit and scope of the invention. All references, patents and patent publications that are identified in this application are incorporated in their entirety herein by reference. The specific example presented below is illustrative only and is not intended to limit the scope of the invention described herein.

EXAMPLE

Experimental Procedures[1]

[1]The abbreviations used are: 3D, three dimensional; EK, enterokinase; FLAG, the peptide whose amino acid is Asp-Tyr-Lys-Asp-Asp-Asp-Asp-Lys, SEQ ID NO. 30; and mMCP, mouse mast cell protease.

Expression of pro-mMCP-6 and pro-EK-mMCP-6-FLAG in Insect Cells—The novel bioengineering approach developed recently to obtain a pseudozymogen form of mMCP-7 that could be proteolytically activated after its purification from the conditioned media of insect cells was used to obtain a similar pseudozymogen (pro-EK-mMCP-6-FLAG) form of mMCP-6. Expressed pro-EK-mMCP-6-FLAG has an EK-susceptible peptide (Asp-Asp-Asp-Asp-Lys, SEQ ID NO. 29) in between the domain that encodes the endogenous pro-peptide and the N-terminal Ile residue of the mature tryptase. The recombinant protein also has the 8-residue FLAG peptide attached to its C terminus. In order for a serine protease to have catalytic activity the α-amino of the N-terminal Ile residue must form a internal ion pair with the carboxyl group of an internal specific Asp residue after the pro-peptide is removed (Freer et al., Biochemistry 1977, 9:1997–2009). Thus, it is critical that mature mMCP-6 have an N-terminal Ile residue. Because EK is a highly specific enzyme that cleaves the Lys-Ile bond in its recognition motif (Light and Janska, Trends Biochem Sci 1989, 14(3):110–112), is a relatively stable enzyme at pH 5.0, and will specifically cleave pro-mMCP-7-FLAG, it was anticipated that pro-mMCP-6-FLAG could be proteolytically activated by EK under conditions where the recombinant tryptase, itself, would have very little enzymatic activity until the pH is raised to 7.0. That the pseudozymogen also has the FLAG peptide at its C-terminus enabled its rapid purification from the insect cell conditioned media by means of an affinity column containing anti-FLAG IgG antibody (Prickett et al., Biotechniques 1989, 7:580–589; Brizzard et al., Biotechniques 1994, 16:730–735).

While, in theory, EK digestion of pro-mMCP-6-FLAG should remove the modified pro-peptide, the resulting recombinant product still will have the FLAG peptide attached to its C-terminus. Nevertheless, it was anticipated that mMCP-6-FLAG would be enzymatically active because the FLAG peptide does not influence the enzymatic activity of mMCP-7.

The relevant cDNA constructs, created using standard polymerase chain reaction approaches, were inserted in the correct orientation into the multiple cloning site of pVL1393 (PharMingen, San Diego, Calif.) downstream of the promoter of the polyhedrin gene. Insect cells were induced to express pro-mMCP-6 and pro-mMCP-6-FLAG, as described previously for pro-mMCP-7 (Matsumoto et al., J. Biol. Chem. 1995, 270:19524–19531) and pro-mMCP-7-FLAG. Briefly, purified plasmid DNA (~5 μg) was mixed with 0.5 μg of linearized BaculoGold™ DNA (PharMingen) and calcium phosphate, each resulting DNA solution was added to 3×10$^6$ adherent Spodoptera frugiperda 9 insect cells (Invitrogen, San Diego, Calif.) that were in their log phase of growth, and the infected cells were cultured for 7 days at 27° C. in medium (Invitrogen) supplemented with 10% heat-inactivated fetal calf serum (Sigma, St. Louis, Mo.). Recombinant virus particles (≧3×10$^7$) from these insect cells were added to a new culture dish containing 6×10$^6$ Trichoplusia ni High Five™ insect cells (Invitrogen) in their log phase of growth, and the infected cells were cultured in serum-free, Xpress medium (BioWhittaker, Walkersville, Md.). Generally 4 d later, the conditioned medium was centrifuged at 1500 g for 15-min at room temperature before attempting to purify the secreted recombinant protein.

Purification of pro-mMCP-6 and pro-EK-mMCP-6-FLAG from Insect Cell Conditioned Media and EK Activation of the Recombinant Zymogen—Pro-mMCP-6 and pro-EK-mMCP-6-FLAG were purified by heparin-Sepharose chromatography, as described for pro-mMCP-7 (Matsumoto et al., J. Biol. Chem. 1995, 270:19524–19531).

The purification of pro-EK-mMCP-6-FLAG also was carried out using an affinity column containing the mouse anti-FLAG M2 monoclonal antibody (Eastman Kodak/International Biotechnol.). This immunoaffinity column (2 ml) was washed with 0.1 M glycine, pH 3.5, and then with 50 mM Tris-HCl and 150 mM NaCl, pH 7.4. After the application of the insect cell conditioned media, the column was washed briefly with the above pH 7.4 buffer, and then bound pro-EK-mMCP-6-FLAG was eluted with 0.1 M glycine, pH 3.5. The eluate was collected into tubes that contained 0.1 M Tris-HCl, pH 7.0, to minimize acid-mediated denaturation of pro-EK-mMCP-6-FLAG. The protein concentration of the eluate was estimated by measuring the absorbance at 280 nm.

Purified pro-EK-mMCP-6-FLAG (~100 μg in 100 μl) was separately mixed with 100 μl of a pH 5.2 buffer consisting of 50 mM sodium acetate and 5 mM calcium chloride. One μl of a solution containing 550 U of calf intestine EK (Biozyme) was added to each, and the mixture was incubated at 37° C. generally for 3 h to allow EK to activate the zymogen in the absence of heparin. The spectrophotometric method of Svendsen and coworkers (Throm. Res. 1972, 1:267–278) was used to determine whether or not mMCP-6-FLAG is enzymatically active. Generally, 1-μl samples of each activation reaction were placed in 1 ml of a pH 7.4 buffer containing 25 mM sodium phosphate, 1 mM EDTA, and 50 μg of tosyl-Gly-Pro-Lys-p-nitroanilide. The change in optical density at 405 nm was then determined after a 3-min incubation at room temperature. The ability of recombinant mMCP-6-FLAG to cleave the trypsin-susceptible substrates tosyl-Gly-Pro-Arg-p-nitroanilide, benzoyl-Ile-Glu-Gly-Arg-p-nitroanilide, benzoyl-Pro-Phe-Arg-p-nitroanilide, and acetyl-Ile-Glu-Ala-Arg-p-nitroanilide were also evaluated.

SDS-PAGE/Immunoblotting and N-terminal Amino Acid Analysis—Insect conditioned media (~20 μl) containing either pro-mMCP-6, pro-EK-mMCP-6-FLAG, or EK-activated mMCP-6-FLAG (~1 μl) were diluted in SDS-PAGE buffer (1% SDS, 5% 2-ME, 0.1% bromophenol blue, and 500 mM Tris-HCl, pH 6.8) and boiled for 5 min before being loaded onto 12% polyacrylamide gels. After SDS-PAGE, the resolved proteins were stained with Coomassie Blue or were transferred in 20 mM Tris-HCl, 150 mM glycine, pH 8.3 buffer containing 20% methanol for 2 to 4 h at 200 mA to PVDF membranes (Millipore) using a BIO-RAD (Richmond, Calif.) immunoblotting apparatus. For immunoanalysis of the resulting protein blots, each membrane was sequentially incubated 1 h in 5% non-fat milk, 1 h with a 1:500 dilution of affinity-purified rabbit anti-mMCP-6 Ig (Ghildyal et al., J. Immunol. 1994, 153:2624–2630) in TBST buffer (Tris-buffered saline with 0.01% Tween 20), TBST buffer alone, and then a 1:1,000 dilution of anti-rabbit IgG alkaline phosphatase conjugate (~1 ng/ml final concentration) in TBST buffer. Immunoreactive proteins were visualized using nitroblue tetrazolium (0.2 mg/ml) and 5-bromo-4-chloro-3-indolyl phosphate (0.1 mg/ml) as substrates.

For N-terminal amino acid analysis, SDS-PAGE-resolved proteins were electrobloted. unto PVDF membranes, briefly stained with 0.5% Ponceau S red (Sigma), and the relevant protein/peptide bands were subjected to automated Edman degradation by the Harvard Microchemistry Facility (Harvard Biological Laboratories, Cambridge, Mass.).

Screening of a Tryptase-Specific, Bacteriophage Peptide Display Library with mMCP-6—A peptide display library that encodes an altered pIII containing at its N terminus the FLAG peptide followed by an 8-residue hypervariable peptide was screened with recombinant mMCP-6-FLAG.

Briefly, phage were obtained that express on their surface a pIII fusion protein with an extension peptide consisting of the FLAG peptide and a hypervariable octamer peptide containing a Lys/Arg residue at the PI site. After the varied phages in the library were allowed to bind to the anti-FLAG IgG column, the immuno-affinity column was incubated with recombinant mMCP-6-FLAG in the presence or absence of heparin. Those phage recovered in the column's eluate were amplified, and the selection procedure was repeated one lo three times. By determining the nucleotide sequence of the relevant portion of the geneIII construct in each clone, the amino acid sequence of the mMCP-6-susceptible peptide in the random domain of the pIII fusion protein was deduced. To prepare the phage column used in the screening process, 10 ml of the phage-enriched supernatant was added to 2 ml of 20% polyethylene glycol (8 kDa; Sigma) and 2.5 M NaCl and the mixture incubated at 4° C. for 30 min. After a 30 min centrifugation at 10,000 g, the recombinant phage in the pellet were resuspended in 2 ml of 150 mM NaCl, 1 mM $NaCl_2$, and 10 mM sodium phosphate, pH 7.0, and applied to a 1-ml affinity column containing the anti-FLAG M1 monoclonal antibody. The column was washed 3 times with 10 ml of the same pH 7.0 buffer to remove unbound phage. EK-activated mMCP-6-FLAG (~50 μg in 200 μl buffer) in the absence or presence of heparin glycosaminoglycan (~50 μg) was added, and the column was sealed and incubated at room temperature for 90 min. After protease treatment, the column was washed with 2 ml of the pH 7.0 buffer to recover those phage which possessed protease-susceptible pIII fusion proteins. Log-phase E. coli were infected with the obtained phage to produce phagemid. Bacteria were again grown in 2×YT medium containing 2% glucose and the phagemid in the bacteria were converted to phage with the addition of helper phage. This screening procedure was repeated up to 4 times to select the phage in the library which are most susceptible to degradation by mMCP-6-FLAG.

E. coli was infected with resulting mMCP-6-FLAG-susceptible phage to generate phagemids. The infected bacteria were seeded onto a plate containing 1.5% agar, 2% Bacto-tryptone, 0.5% Bacto-yeast extract, 2% glucose, 0.09 M NaCl, 0.01 M $MgCl_2$, and 100 μg/ml ampicillin. Individual clones were isolated and grown overnight at 37° C. in 2 ml of 2×YT medium containing 2% glucose with 50 μg/ml ampicillin. One ml of the overnight cultures were centrifuged at ~12,000 g for 5 min. The bacteria in the pellets were lysed and the DNAs were extracted with mini-prep method. The DNAs were digested with NotI and EcoRI restriction enzymes at 37° C. overnight. The digested DNA mini-preps were subjected to electrophoresis on a 1% agarose gel, and those individual phage clones with ~1300-bp inserts were selected for maxi-preparation of their DNAs using nucleo-bond DNA-binding columns (The Nest Group). The nucleotide sequences which encode the 8-mer, protease-susceptible peptide domains in the fusion proteins were determined.

In Vitro Degradation of Fibronectin by Recombinant mMCP-6-FLAG—Five μg of purified mouse fibronectin (Alexis) was suspended in 1 mM EDTA and 25 mM sodium phosphate, pH 7.4, containing 0.01 U EK, 0.5 μg recombinant pro-EK-mMCP-6-FLAG, 0.5 μg recombinant mMCP-6-FLAG (activated with 0.01 U EK), or 0.5 μg recombinant mMCP-7FLAG (activated with 0.01 U EK). After an incubated for various lengths of times, the resulting digests were subjected to SDS-PAGE. In one experiment, the N-terminal amino acid sequences; of the major fibronectin fragments in the mMCP-FLAG digest were determined.

mMCP-6-FLAG-Induced Emigration of Neutrophils Into the Peritoneal Cavity and mMCP-6-Induced Growth of Fibroblasts and their Adhesion to Fibronectin—This experiment is discussed below.

Results and Discussion

Generation of pro-mMCP-6 and pro-EK-mMCP-6-FLAG in Insect Cells, and EK Conversion of the Recombinant Pseudozymogen to Enzymatically Active Tryptase—Insect cells infected with the relevant construct secreted large amounts of pro-mMCP-6 and pro-EK-mMCP-6-FLAG into the conditioned media. Based on its deduced amino acid sequence, mMCP-6 has an overall net charge at pH 7.0 that is considerably more negative than any mouse mast cell chymase (Šali et al., J. Biol. Chem. 1993, 268:9023–9034). Nevertheless, because mMCP-6 does not dissociate easily from its serglycin proteoglycan, it is retained for >1 h in inflammatory sites (Ghildyal et al., J. Exp. Med. 1996, 184:1061–1073). Modeling studies suggested that this, unexpected feature of mMCP-6 is caused by an Arg/Lys rich domain that forms on the surface when the tryptase is properly folded. Like pro-mMCP-6, pro-EK-mMCP-6-FLAG bound to a heparin-Sepharose column that had been equilibrated in 100 mM NaCl/10 mM sodium phosphate, pH 5.5. Because both recombinant proteins dissociated from the heparin-Sepharose affinity column when the NaCi concentration of the buffer was raised to >300 mM, it was concluded that the secreted mMCP-6 pseudozymogen is properly folded. Pro-EK-mMCP-6-FLAG also could be readily purified using the immunoaffinity column.

As assessed by SDS-PAGE, the recombinant pseudozymogen decreased ~2 kDa in size when incubated for 3 to 24 h with EK. Amino acid sequence analysis revealed that the resulting product possessed an N-terminal sequence of X-Y-Z which is identical to that of mature mMCP-6 deduced from its cDNA (Reynolds et al., J. Biol. Chem. 1991, 266:3847–3853). While recombinant and native mMCP-7 exhibit good catalytic activity in the absence of heparin (Ghildyal et al., J. Exp. Med. 1996, 184:1061–1073), it has been reported that human mast cell tryptases purified from the lung do not exhibit substantial enzymatic activity unless this glycosaminoglycan is present in the assay (Schwartz and Bradford, J. Biol. Chem. 1986, 261:7372–7379; Alter et al., Biochem. J. 1987, 248:821–827). The ability to purify pro-EK-mMCP-6-FLAG from the conditioned media by means of the immuno-affinity column allowed us to determine if the recombinant protease exhibits enzymatic activity in the absence of heparin. Recombinant mMCP-6-FLAG exhibited optimal enzymatic activity at ~pH 7.4 and good enzymatic activity after a 3-h incubation with EK at 37° C. at pH 5.2.

The finding that the EK-activated tryptase readily cleaves tosyl-Gly-Pro-Lys-p-nitroanilide and tosyl-Gly-Pro-Arg-p-nitroanilide in the absence of heparin, indicates that the broad catalytic activity of this tryptase is not dependent on heparin-containing serglycin proteoglycans. However, the observation that mMCP-6-FLAG in the presence or absence of heparin, does not effectively cleave benzoyl-Ile-Glu-Gly-Arg-p-nitroanilide, benzoyl-Pro-Phe-Arg-p-nitroanilide, or acetyl-Ile-Glu-Ala-Arg-p-nitroanilide indicates that mMCP-6 has a more restricted substrate specificity than trypsin. Models of the three-dimensional (3D) structures of mMCP-6 and mMCP-7 (Matsumoto et al., J. Biol. Chem. 1995, 270:19524–19531; Ghildyal et al., J. Exp. Med. 1996, 184:1061–1073) based on the crystallographic structure of bovine pancreatic trypsin suggests that seven loops form the substrate-binding cleft of each tryptase, as occurs for other serine proteases (Perona and Craik, Protein Sci. 1995;

4:2337–360). Relative to trypsin, 3 of the 7 loops in mMCP-7 have insertions that make its substrate-binding cleft deeper and more restricted than that of trypsin. Because similar insertions are found in the corresponding loops of mMCP-6, it is not surprisingly that this latter serine protease also has a restricted substrate specificity.

mMCP-6-Induced Emigration of Neutrophils Into the Peritoneal Cavity of BALB/c Mice—The mast cells that reside in the peritoneal cavity of BALB/c mice express mMCP-6 but not mMCP-7 (Stevens et al., Proc. Natl. Acad. Sci. USA 1994, 91:128–132). Because this observation suggests that mMCP-6, but not mMCP-7, cleaves specific proteins that reside in the peritoneal cavity, enzymatically active mMCP-6-FLAG was injected into the peritoneal cavity to assess whether or not the tryptase can induce an inflammatory reaction. Six to 36 h after mMCP-6-FLAG administration, a pronounced influx of neutrophils was observed in the peritoneal cavity. As typically seen in acute inflammatory responses (Robbins et al., "Inflammation and repair" in *Pathologic Basis of Disease*. 1994, 5th ed., W. B. Saunders Co., Philadelphia, Pa., pp 57–60), large numbers of eosinophils, lymphocytes, erythrocytes, basophils, and platelets, were not detected in the peritoneal exudate of the treated mice. However, unlike a typical inflammatory response where monocytes and eosinophils predominant at subsequent time points (Robbins et al., supra), kinetic experiments revealed that the mMCP-6-induced neutrophilia persisted for at least 3 days. Thus, the direct or indirect chemotaxis activity of mMCP-6 is relatively neutrophil specific. It also appears that tryptase treatment results in a relatively persistent recruitment of neutrophils into the peritoneal cavity. The observation that pro-mMCP-6-FLAG does not induce neutrophil emigration at the 36 h time point indicates that the induced inflammatory reaction is dependent on enzymatically active mMCP-6. Moreover, the observation that enzymatically active mMCP-7-FLAG 7-FLAG has very little, if any, neutrophil chemotaxis activity in this in vivo assay also documents the exquisite specificity of the tryptase effect.

Screening of a Tryptase-Specific Phage Display Peptide Library with Recombinant mMCP-6-FLAG—The observation that recombinant mMCP-7-FLAG cleaves acetyl-Ile-Glu-Ala-Arg-p-nitroanilide much better than mMCP-6-FLAG in vitro and that mMCP-6-FLAG selectively induces neutrophil emigration in vivo indicates that the two mouse tryptases have different substrate specificities even though their overall amino acid sequences are quite similar. Thus, the tryptase-specific, phage peptide display library that helped us identify a physiologic substrate of mMCP-7 (Huang, et al., J Biol Chem. 1997, 272:31885–31893) was used to identify mMCP-6-preferred peptide substrates. When the library was subjected to 4 rounds of treatment with enzymatically-active mMCP-6-FLAG in the absence of heparin glycosaminoglycan, no specific peptide sequence in the hypervariable domain of the pIII fusion protein was obtained in the 30 arbitrarily selected clones (Table I). Nevertheless, the observation that only one of these mMCP-6-susceptible clones had the preferred mMCP-7-susceptible sequence in its pIII fusion protein (Huang, et al., J Biol Chem. 1997, 272:31885–31893) was further evidence that the two homologous tryptases degrade very different substrates. Another family of serine protease genes is present on chromosome 14 that encode cathepsin G (Heusel et al., Blood 1993, 81:614–1623), at least 5 granzymes (Burnet et al., Nature 1986, 322:268–271; Pham et al., Proc. Natl. Acad. Sci. USA 1996, 93:13090–13095), and at least 6 mast cell chymases (Gurish et al., J Biol Chem. 1993, 268:11372–11379; Hunt et al., J. Biol. Chem. 1995, 271:2851–2855). The observation that the two mouse tryptases are very similar in their overall primary sequences but very different in their preferred peptide substrates is further support that the chromosome 14 and chromosome 17 complexes of serine protease genes evolved so that mast cells and other hematopoietic effector cells that express varied members of the two families of serine proteases degrade different panels of proteins.

TABLE I mMCP-6-susceptible peptides obtained in the absence of heparin

The tryptase-specific, phage peptide display library was incubated 4 times with recombinant mMCP-6-FLAG in the absence of heparin. Clones were isolated and the deduced amino acid sequences of the peptides found in protease-susceptible domains of the pIII fusion protein were deduced.

| Clones | Amino Acid Sequence of Peptide | |
|---|---|---|
| 2 | Val-Arg-Pro-Val-Lys-Ser-Phe-Arg | (SEQ. ID NO. 31) |
| 1 | Ser-Leu-Ser-Ser-Arg-Gln-Ser-Pro | (SEQ. ID NO. 32) |
| 1 | Ser-Pro-Arg-Pro-Arg-Ser-Thr-Pro | (SEQ. ID NO. 33) |
| 1 | Gln-Arg-Thr-Lys-Arg-Lys-His-Asn | (SEQ. ID NO. 34) |
| 1 | Gly-Pro-Arg-Leu-Arg-His-Pro-Arg | (SEQ. ID NO. 35) |
| 1 | Asn-Leu-Arg-Lys-Arg-Lys-Ile-Lys | (SEQ. ID NO. 36) |
| 1 | Asn-Ser-Thr-Val-Arg-Lys-Arg-Lys | (SEQ. ID NO. 37) |

TABLE I-continued mMCP-6-susceptible peptides obtained in the absence of heparin

The tryptase-specific, phage peptide display library was incubated 4 times with recombinant mMCP-6-FLAG in the absence of heparin. Clones were isolated and the deduced amino acid sequences of the peptides found in protease-susceptible domains of the pIII fusion protein were deduced.

| Clones | Amino Acid Sequence of Peptide | |
|---|---|---|
| 1 | Pro-Pro-Pro-Phe-Arg-Arg-Ser-Ser | (SEQ. ID NO. 38) |
| 1 | Pro-Leu-Ile-Leu-Arg-Ser-Arg-Ala | (SEQ. ID NO. 39) |
| 1 | Lys-Lys-Ile-Glu-Arg-Arg-Asn-Thr | (SEQ. ID NO. 40) |
| 1 | Gln-Lys-Arg-Gly-Arg-Glu-Pro-Arg | (SEQ. ID NO. 41) |
| 1 | Glu-Glu-Lys-Lys-His-Lys-Lys | (SEQ. ID NO. 42) |
| 1 | Arg-Gln-Asn-Arg-Arg-Pro-Ser-Asn | (SEQ. ID NO. 43) |
| 1 | Val-Arg-Pro-Ala-Arg-Ala-Leu-His | (SEQ. ID NO. 44) |
| 1 | Leu-Ile-Ala-Leu-Arg-Ser-Thr-Thr | (SEQ. ID NO. 45) |
| 1 | Pro-Thr-Pro-Leu-Lys-His-Pro-Arg | (SEQ. ID NO. 46) |
| 1 | Pro-Tyr-Pro-Pro-Lys-Arg-Thr-Pro | (SEQ. ID NO. 47) |
| 1 | Leu-Ser-Thr-Ser-Arg-Ala-Ser-Ile | (SEQ. ID NO. 48) |
| 1 | Thr-Gly-Val-His-Lys-Pro-Ser-Thr | (SEQ. ID NO. 49) |
| 1 | Leu-Cys-Ala-Lys-Arg-Leu-Tyr-Arg | (SEQ. ID NO. 50) |
| 1 | Arg-Lys-Pro-Thr-Lys-Lys-Asn-Ser | (SEQ. ID NO. 51) |
| 1 | Glu-Cys-Arg-Gln-Arg-His-Thr-Arg | (SEQ. ID NO. 52) |
| 1 | Ser-Leu-Ala-Leu-Arg-Val-Trp-Arg | (SEQ. ID NO. 53) |
| 1 | Gly-Pro-Arg-Leu-Arg-His-Pro-Arg | (SEQ. ID NO. 54) |
| 1 | Phe-Ile-Ser-Arg-Arg-Val-Cys-Arg | (SEQ. ID NO. 55) |
| 1 | Pro-Asp-Asn-Gln-Arg-Tyr-Ile-Thr | (SEQ. ID NO. 56) |
| 1 | Pro-Leu-Pro-Cys-Lys-Leu-Asp-Ala | (SEQ. ID NO. 57) |
| 1 | Ile-Arg-Phe-Ala-Arg-Ser-Gln-Ala | (SEQ. ID NO. 58) |
| 1 | Pro-Thr-Pro-Leu-Lys-His-Pro-Arg | (SEQ. ID NO. 59) |

The two most prominent features of the peptides obtained by screening the library with mMCP-6-FLAG alone were the over and under representation of positively and negatively charged residues, respectively. One half of the selected clones had 3 or more Lys and/or Arg residues in the susceptible peptide, and 2 of the clones actually had 5 positively charged residues. These findings are consistent with the electrostatic properties of the mMCP-6 model which revealed that the substrate-binding pocket of mMCP-6 is more negatively charged than that in mMCP-7 (Ghildyal et al., J. Exp. Med. 1996, 184:1061–1073). The difference in the electrostatic potential of the pocket is due primarily to loop 3 which has a −3 net charge in mMCP-6 and a 0 net charge in mMCP-7.

When the phage peptide display library was subjected to 2 to 4 rounds of treatment with mMCP-6-FLAG in the presence of an equal amount of heparin glycosaminoglycan, a more limited number of sequences were obtained (Table II). Surprisingly, the 2 clones that were obtained repeatedly had dissimilar sequences of Thr-Pro-Leu-Leu-Lys-Ser-Trp-Leu (SEQ. ID NO. 64) and Arg-Asn-Arg-Gln-Lys-Thr-Asn-Asn (SEQ. ID NO. 65). The latter favored peptides and the other less favored peptides obtained in this selection process were similar in that each had a Pro residue, at least one Thr or Ser residue, and a net charge of only +1 or +2. The discovery that the favored peptide in this series had a Pro residue at its P4 site is of interest because Cromlish and coworkers (1987) found that a human mast cell tryptase purified from the pituitary will cleave three prohormones ex vivo that have Pro residues at their P4 sites and Lys/Arg residues at their P1 sites.

TABLE II mMCP-6-susceptible peptides obtained in the presence of heparin

The tryptase-specific, phage peptide display library was incubated 2 (A) or 4 (B) times with recombinant mMCP-6-FLAG in the presence of an equal weight amount of heparin. Clones were isolated and the deduced amino acid sequences of the peptides found in protease-susceptible domains of the pIII fusion protein were deduced.

| Clones | Amino Acid Sequence of Peptide | |
|---|---|---|
| A. Two Rounds of Treatment | | |
| 1 | Pro-Phe-Thr-His-Lys-Ser-Leu-Ser | (SEQ. ID NO. 60) |
| 1 | Ser-Val-Leu-Pro-Lys-Leu-Arg-Ile | (SEQ. ID NO. 61) |
| 1 | Pro-Lys-Glu-Thr-Lys-Gln-Thr-Asn | (SEQ. ID NO. 62) |
| 3 | Ser-Leu-Ser-Ser-Arg-Gln-Ser-Pro | (SEQ. ID NO. 63) |
| 5 | Thr-Pro-Leu-Leu-Lys-Ser-Trp-Leu | (SEQ. ID NO. 64) |
| 11 | Arg-Asn-Arg-Gln-Lys-Thr-Asn | (SEQ. ID NO. 65) |
| B. Four Rounds of Treatment | | |
| 1 | Pro-Lys-Glu-Thr-Lys-Gln-Thr-Asn | (SEQ. ID NO. 62) |
| 1 | Ser-Val-Leu-Pro-Lys-Leu-Arg-Ile | (SEQ. ID NO. 61) |
| 2 | Ser-Leu-Ser-Ser-Arg-Gln-Ser-Pro | (SEQ. ID NO. 63) |
| 4 | Arg-Asn-Arg-Gln-Lys-Thr-Asn-Asn | (SEQ. ID NO. 65) |
| 7 | Thr-Pro-Leu-Leu-Lys-Ser-Trp-Leu | (SEQ. ID NO. 64) |

Despite these interesting findings, we speculated that the favored peptide from the phage display library which possesses a +3 charge probably is more physiologically relevant because its overall charge is similar to that generally obtained when the library was screened with mMCP-6 alone. Why only one +3 positively charged peptide was obtained and why this peptide was not present in the original 30 clones isolated when the library was screened with mMCP-6 alone remains to be determined experimentally. However, the electrostatic potential of the 3D model of mMCP-6 suggests that the putative heparin-binding domain on the surface of this tryptase resides closer to its active site than in all other mMCPs. Thus, it is likely that heparin sterically restricts the substrate-binding cleft of mMCP-6 by directly influencing one of the 7 loops that form the pocket. The discovery that the substrate specificity of a rat mast cell chymase is also altered by heparin (Le Trong et al., Proc. Natl. Acad. Sci. USA 1987, 84:364–367) now emphasizes the importance of serglycin proteoglycans in fine tuning the substrate specificities of certain members of the chromosome 14 and chromosome 17 families of serine proteases.

A computer search of a protein database with the sequence Arg-Asn-Arg-Gln-Lys-Thr (SEQ. ID NO. 1) present in the positively charged peptide revealed that a nearly identical sequence (i.e., Arg-Gly-Arg-Gln-Lys-Thr, SEQ. ID NO. 11) resides in the middle of each subunit of fibronectin and that this sequence is conserved from rats to humans. Fibronectin is an abundant protein in plasma and varied extracellular matrices and plays a central role in cellular adhesion. This adhesion protein is a dimer consisting of ~220-kDa polypeptides that are disulfide bonded at the C terminus (Komblihtt et al., EMBO J. 1985, 4:1755–1759; Skorstengaard et al., Eur. J. Biochem. 1986, 161:441–453). Its primary structure can vary somewhat due to differential splicing of the transcript but each subunit consists of nearly 2400 residues. These subunits possess numerous conserved domains that enable fibronectin to interact simultaneously with different proteins on the cell's surface and in the extracellular matrix. For example, a domain near the N-terminus binds to varied native and denatured collagens, whereas the C-terminal half of the fibronectin contains adjacent domains that allow fibronectin to interact simultaneous with varied integrins and proteoglycans on the surface of the cell. In the case of fibroblasts, fibronectin forms focal adhesions with $\beta_1$ integrins and syndecan proteoglycans thereby inducing synergistic signaling through distinct pathways (Woods and Couchman, Mol. Biol. Cell 1994, 5:183–192; Couchman and Woods, J. Cell. Biochem. 1996, 61:578–584). The in vitro adhesion of melanoma cells to fibronectin is also mediated by the cooperative action of $\beta_1$ integrins and cell surface proteoglycans (Iida et al., J. Cell Biol. 1992, 118:431–444; Wahl et al., J. Leukocyte Biol. 1996, 59:789–796). The mMCP-6-susceptible sequence in fibronectin is at residues 1351 to 1356 between the collagen and integrin binding domains. Thus, the specific cleavage at this site should have a dramatic effect on the fibronectin-mediated adhesion of fibroblasts.

In Vitro Digestion of Fibronectin and Disruption of Fibronectin-Mediated Adhesion of Fibroblasts by mMCP-6-FLAG—Fibronectin was readily cleaved by the mMCP-6-FLAG/heparin complex in vitro but not by mMCP-7-FLAG either in the presence or absence of heparin.

Fibronectin is susceptible to cleavage by a wide range of neutral proteases, including chymotrypsin (Ehrismann et al., J. Biol. Chem. 1982, 257:7381–7387), trypsin (Mosher and Proctor, Science 1980, 209:927–929), α-thrombin (Furie and Rifkin, J. Biol. Chem. 1980, 255:3134–3140), plasmin (Jilek and Hörmann, Hoppe-Seyler's Z. Physiol. Chem. 1977, 358:133–136), plasminogen activator (Quigley et al., Proc. Natl. Acad. Sci. USA 1987, 84:2776–2780), cathepsin G (Vartio et al., J. Biol. Chem. 1981, 256:471–477), urokinase (Gold et al., Biochem. J. 1989, 262:529–534), elastase (McDonald and Kelley, J. Biol. Chem. 1980 255:8848–8858), and mast cell chymases (Vartio et al., J. Biol. Chem. 1981, 256:471–477). Because of its exquisite protease-susceptibility, fibronectin is routinely used to assess general neutral protease activities in samples. BALB/c mouse bone marrow-derived mast cells, developed in vitro using T cell-conditioned media, possess serine proteases in their granules that can readily degrade human fibronectin in vitro (DuBuske et al., J. Immunol. 1984, 133:1535–1541) into 8 or more fragments. Because this population of mast cells expresses mMCP-2 (Ghildyal et al., J. Biol. Chem. 1992, 267:8473–8477), mMCP-5 (McNeil et al., Proc. Natl. Acad. Sci. USA 1991, 89:11174–11178), mMCP-6 (Reynolds et al., J. Biol. Chem. 1991, 266:3847–3853 ), and mMCP-7 (McNeil et al., supra), it has not been ascertained which, if any, of these granule mMCPs degrade fibronectin in vitro. There are nearly 200 positively charged (Arg+Lys) residues in each subunit of fibronectin. Thus, it is not much of a surprise that this adhesion protein is susceptible to digestion by recombinant mMCP-6-FLAG. The novel finding is the specificity of the enzymatic attack when mMCP-6-FLAG is bound to heparin. Only 2 fragments are obtained after a 60-min incubation of fibronectin with mMCP-6-FLAG. N-terminal amino acid analysis of the amino acid sequence of the generated fragments is used to confirm that the preferred cleavage site in fibronectin is Arg-Gly-Arg-Gln-Lys-Thr (SEQ. ID NO. 11).

Swiss albino mouse skin-derived 3T3 fibroblasts exhibit homotypic, contact inhibition in vitro. However, these cells will become less adhesive and divide in vitro when they are trypsin treated. To determine if mMCP-6-FLAG could specifically alter the growth and/or adhesion of these cells, the fibroblasts were allowed to attach to replicate fibronectin-coated culture dishes and then were incubated for 15 min at 37° C. with buffer alone or buffer containing either pro-EK-mMCP-6-FLAG, mMCP-6-FLAG, mMCP-7-FLAG, or trypsin. The fibroblasts which were exposed to buffer alone, pro-EK-mMCP-6-FLAG, or mMCP-7-FLAG continued to adhere to the fibronectin-coated culture dishes. Many of the cells in these cultures also exhibited the classical stellate shape of a fibroblast bound to its matrix via focal adhesion sites. In contrast, both trypsin and mMCP-6-FLAG rapidly induced the cultured fibroblasts to round up. Moreover, very few fibroblasts remained attached to the culture dish after a 40 min incubation with either protease. SDS-PAGE/immunoblot analysis of the supernatants from the result cultures confirmed that fibronectin was degraded in the mMCP-6-FLAG-treated cultures but not in the pro-EK-mMCP-6-FLAG or mMCP-7-FLAG treated cultures.

Although Forsberg-Nilsson and coworkers (Scand. J. Immunol. 1996, 44:267–272) recently reported that a mast cell tryptase purified from human lung is not mitogenic for cultured human foreskin fibroblasts, Ruoss and coworkers (J. Clin. Invest. 1991, 88:493–499) reported that a tryptase purified from dog mastocytoma tissue is mitogenic for cultured Chinese hamster lung fibroblasts. Hartman and coworkers (Am. J. Physiol. 1992, 262:L528–L534 ) reported that a tryptase purified from human lung is mitogenic for cultured rat, hamster, and human fibroblasts but not for rat smooth muscle cells, and Cairns and Walls (J. Immunol. 1996, 156:275–283) reported that tryptases purified from human lung is mitogenic for the H292 human epithelial cell line. Mast cells express two or more tryptases in all species that have been examined. Moreover, strain-dependent expression of tryptase expression has been noted in mast cells of the mouse (Ghildyal et al., J. Immunol. 1994, 153:2624–2630; Hunt et al., J. Biol. Chem. 1996, 271:2851–2855) and rat (Lützelschwab et al., J. Exp. Med. 1996, 185:13–29). The discovery that mMCP-7-FLAG treated mouse fibroblasts do not lose their contact inhibition, continue to adhere to fibronectin, and do not increase their rate of proliferation, suggests that the apparently conflicting data in the above human studies probably is the result of functionally different tryptases in the analyzed preparations.

The mechanism by which the dog and human mast cell tryptases induce proliferation of fibroblasts and epithelial cells in vitro was not deduced in the Ruoss et al. (J. Clin. Invest. 1991, 88:493–499), Hartmann et al. (Am. J. Physiol. 1992, 262:L528–L534), and Cairns and Walls (J. Immunol. 1996, 156:275–283) studies but it appears that they do not stimulate cellular division via the thrombin receptor. While it is now well established that fibronectin plays a central role in cell adhesion, it has become increasingly apparent that certain proteolytically-derived fragments of fibronectin possess potent bioactivities in some in vitro systems. For example, the C-terminal 140- to 120-kDa fragment of fibronectin that presumably contains both its integrin- and syndecan-binding domains induces expression of certain metalloproteases and their inhibitors in fibroblasts and other cell types (Werb et al., J. Cell Biol. 1989, 109:877–889; Huhtala et al., J. Cell Biol. 1995, 129:867–879 ; Kapila et al., Matrix Biol. 1996, 15:251–261). Relevant to our study, it has been shown that comparable fragments of fibronectin are chemotactic for fibroblasts (Seppa et al., Cell Biol. Int. Reports 1981, 5:813–819) and neutrophils (Odekon et al., Immunol. 1991, 74:114–120). The discovery that neutrophils are selectively recruited into the peritoneal cavity of BALB/c mice when recombinant mMCP-6-FLAG, but not recombinant mMCP-7-FLAG, is injected into this site, now suggests that the neutrophil emigration in this in vivo assay is mediated, in part, by a generated large-sized fragment of fibronectin that lacks its collagen binding domain. Thus, our discovery that the tryptase mMCP-6 (but not the tryptase mMCP-7) specifically cuts fibronectin between its collagen- and integrin-binding domains has important implications for mast cell-mediated control of fibrosis and inflammation.

Although mMCP-6 and mMCP-7 have different substrate specificities, both tryptases alter integrin-mediated signaling pathways. mMCP-7 does this by attacking fibrinogen which is the ligand for the $\alpha_M\beta_2$, $\alpha_X\beta_2$, $\alpha_{IIb}$, $\beta_3$, and $\alpha_V\beta_3$, family of integrins (Springer Nature 1990, 346:425–434; Wahl et al., J. Leukocyte Biol. 1996, 59:789–796), whereas mMCP-6 does this by attacking fibronectin which is the ligand for the $\alpha_2\beta_1$, $\alpha_3\beta_1$, $\alpha_4\beta_1$, $\alpha_5\beta_1$, $\alpha_V\beta_1$, $\alpha_{IIb}\beta_3$, $\alpha_V\beta_3$, and $\alpha_4\beta_7$ family of integrins (Springer, supra; Wahl et al., supra) Although their roles in asthma have not been deduced, linkage analysis (De Sanctis et al., Nature Genetics 1995, 11:150–154) has implicated the region of chromosome 17 where the mMCP-6 and mMCP-7 genes reside as one of three candidate loci for the inheritance of intrinsic airway hyperresponsiveness. In addition, low molecular weight inhibitors of tryptic enzymes block antigen-induced airway constriction and tissue inflammatory response in Ascaris suum-sensitized sheep (Clark et al., Am. J. Respir. Crit. Care Med. 1995, 152:2076–2083). Our data suggest that mast cell tryptases play central roles in mast cell-mediated inflammation by controlling different integrin-dependent signaling pathways.

TABLE III presented below includes references to the GenBank Accession numbers of selected sequences presented in the Sequence Listing, followed by the claims and the abstract.

TABLE III

SEQ ID NO:12 is the amino acid sequence of fibronectin (GenBank No. 279675)
SEQ ID NO:13 is the nucleotide sequence of mMCP-6 (GenBank No. M57625, Reynolds, et al., J. Biol. Chem. 1991, 266:3847–3853).
SEQ ID NO:14 is the nucleotide sequence of mMCP-6 (GenBank No. M57626, Reynolds, et al., J. Biol. Chem. 1991, 266:3847–3853).

TABLE III-continued

SEQ ID NO:15 is the deduced amino acid sequence of the mMCP-6 zymogen (GenBank Nos. M57625 and M57626, Reynolds, et al., J. Biol. Chem. 1991, 266:3847–3853).
SEQ ID NO:16 is the nucleic acid sequence of human mast cell tryptase α: (GenBank No. M30038).
SEQ ID NO:17 is the deduced amino acid sequence of human mast cell tryptase α (GenBank No. M30038).
SEQ ID NO:18 is the nucleic acid sequence of human mast cell tryptase I (GenBank No. M33491).
SEQ ID NO:19 is the deduced amino acid sequence of human mast cell tryptase I (GenBank No. M33491).
SEQ ID NO:20 is the nucleic acid sequence of human mast cell tryptase II/β (GenBank No. M33492).
SEQ ID NO:21 is the deduced amino acid sequence of human mast cell tryptase II/β (GenBank No. M33492).
SEQ ID NO:22 is the nucleic acid sequence of human mast cell tryptase III (GenBank No. M33493).
SEQ ID NO:23 is the deduced amino acid sequence of human mast cell tryptase III (GenBankNo. M33493).
SEQ ID NO:24 is the nucleic acid sequence of the rat homolog of mMCP-6 (GenBank No. U67909)

We claim:

1. A peptide selected from the group consisting of:

Arg-Asn-Arg-Gln-Lys-Thr (SEQ.ID NO.1), Arg-Asn-Arg (SEQ.ID NO.2), Arg-Asn-Arg-Gln (SEQ.ID NO.3), Arg-Asn-Arg-Gln-Lys (SEQ.ID NO.4), Asn-Arg-Gln-Lys-Thr(SEQ.ID NO.5), Arg-Gln-Lys-Thr (SEQ.ID NO.6), Gln-Lys-Thr (SEQ.ID NO.7), Arg-Gln-Lys (SEQ.ID NO.8), Asn-Arg-Gln (SEQ.ID NO.9), and Arg-Gln-Lys (SEQ.ID NO.10).

2. The peptide of claim 1, wherein said peptide is selected from the group consisting of: Arg-Asn-Arg (SEQ.ID NO.2), Arg-Asn-Arg-Gln (SEQ.ID NO.3), Arg-Asn-Arg-Gln-Lys (SEQ.ID NO.4), Asn-Arg-Gln-Lys-Thr (SEQ.ID NO.5), Arg-Gln-Lys-Thr (SEQ.ID NO.6), Gln-Lys-Thr (SEQ.ID NO.7), Arg-Gln-Lys (SEQ.ID NO.8), Asn-Arg-Gln (SEQ.ID NO.9), and Arg-Gln-Lys (SEQ.ID NO.10).

3. The peptide of claim 1, wherein said peptide contains 1, 2, 3, 4, or 6 conservative amino acid substitutions, provided that the number of conservative amino acid substitutions cannot exceed the number of amino acids in the peptide.

4. The peptide of claim 1, wherein the amino acids are covalently coupled by non-hydrolyzable peptide bonds.

5. A tryptase-6 complex inhibitor that is a functionally equivalent peptide of SEQ.ID NO. 1, said functionally equivalent peptide having the formula:

X-P-Y, wherein:

P is a peptide selected from the peptides of claims 1, 2, 3, or 4;

X is an N-terminal peptide containing from zero to five amino acids of N-terminal to amino acids 1351–1356 of SEQ.ID NO. 12;

Y is a C-terminal peptide containing from zero to five amino acids of C-terminal to amino acids 1351–1356 of SEQ.ID NO. 12;

wherein said functionally equivalent peptide competitively inhibits cleavage of a peptide having SEQ.ID NO. 1 by the tryptase-6 complex.

6. The tryptase-6 complex inhibitor of claim 5, wherein the tryptase-6 complex is a human tryptase-6 complex.

7. A method for selecting a tryptase-6 complex inhibitor comprising:

determining whether a tryptase-6 complex cleaves a peptide that is or that contains the amino acid sequence of SEQ.ID NO. 1 in the presence of a putative tryptase-6 complex inhibitor.

8. The method of claim 6, wherein the tryptase-6 complex is a human tryptase-6 complex.

9. The method of claim 6, wherein the tryptase-6 complex is an mMCP-6 complex.

10. The method of claim 6, wherein the tryptase-6 complex protease inhibitor is contained in a phage display library.

11. A peptide having the sequence:

Arg-Asn-Arg-Gln-Lys-Thr (SEQ.ID NO. 1) and functionally equivalent fragments thereof that contain from 3 to 6 amino acids and wherein said functionally equivalent fragments competitively inhibit cleavage of a peptide having SEQ.ID NO. 1 by a tryptase-6 complex.

12. The peptide of claim 10, wherein said peptide is SEQ.ID NO. 1.

13. The peptide of claim 10, wherein said peptide is SEQ.ID NO. 2.

14. The peptide of claim 10, wherein said peptide is SEQ.ID NO. 3.

15. The peptide of claim 10, wherein said peptide is SEQ.ID NO. 4.

16. The peptide of claim 10, wherein said peptide is SEQ.ID NO. 5.

17. The peptide of claim 10, wherein said peptide is SEQ.ID NO. 6.

18. The peptide of claim 10, wherein said peptide is SEQ.ID NO. 7.

19. The peptide of claim 10, wherein said peptide is SEQ.ID NO. 8.

20. The peptide of claim 10, wherein said peptide is SEQ.ID NO. 9.

21. The peptide of claim 10, wherein said peptide is SEQ.ID.NO. 10.

* * * * *